United States Patent
Moffat, IV

(10) Patent No.: US 12,239,845 B2
(45) Date of Patent: *Mar. 4, 2025

(54) PHOTOTHERAPEUTIC APPARATUS FOR FOCUSED UVB RADIATION AND VITAMIN D SYNTHESIS AND ASSOCIATED SYSTEMS AND METHODS

(71) Applicant: BeneSol, Inc., Bainbridge Island, WA (US)

(72) Inventor: William A. Moffat, IV, Bainbridge Island, WA (US)

(73) Assignee: BENESOL, INC., Bainbridge Island, WA (US)

( * ) Notice: Subject to any disclaimer, the term of this patent is extended or adjusted under 35 U.S.C. 154(b) by 623 days.

This patent is subject to a terminal disclaimer.

(21) Appl. No.: 17/315,682

(22) Filed: May 10, 2021

(65) Prior Publication Data

US 2021/0260402 A1 Aug. 26, 2021

Related U.S. Application Data

(60) Continuation of application No. 16/262,682, filed on Jan. 30, 2019, now Pat. No. 11,007,376, which is a
(Continued)

(51) Int. Cl.
*A61N 5/06* (2006.01)

(52) U.S. Cl.
CPC .......... *A61N 5/0616* (2013.01); *A61N 5/0613* (2013.01); *A61N 2005/0615* (2013.01);
(Continued)

(58) Field of Classification Search
CPC ................ A61N 5/0616; A61N 5/0613; A61N 2005/0627; A61N 2005/064; A61N 2005/0652
See application file for complete search history.

(56) References Cited

U.S. PATENT DOCUMENTS 5,265,598 A 11/1993 Searfoss et al.
5,531,664 A 7/1996 Adachi et al.
(Continued)

FOREIGN PATENT DOCUMENTS

CN 101045177 10/2007
CN 101548895 10/2009
(Continued)

OTHER PUBLICATIONS

"Asahi Spectra Optical Filters," https://web.archive.org/web201005 1608304/http://www.asahispectra.com/opticalfilters/uv_bandpass_filter.html; archive of website from 2010, 2 pages.
(Continued)

*Primary Examiner* — Joseph M Dietrich
(74) *Attorney, Agent, or Firm* — Perkins Coie LLP

(57) ABSTRACT

The present disclosure is directed to a phototherapeutic apparatus for focused UVB radiation and vitamin D synthesis and associated systems methods. In one embodiment a phototherapeutic apparatus can include a housing at least partially defining an irradiation zone, and an ultraviolet (UV) radiation source carried by the housing. The irradiation zone can be configured to accommodate at least a portion of a human patient. The phototherapeutic apparatus can further include a filter between the UV radiation source and the irradiation zone. The filter can be configured to at least substantially remove UV radiation outside of a predetermined spectrum centered at about 297 nm and having a bandwidth of at most 10 nm.

20 Claims, 12 Drawing Sheets

Related U.S. Application Data division of application No. 13/733,860, filed on Jan. 3, 2013, now Pat. No. 10,226,641.

(60) Provisional application No. 61/582,778, filed on Jan. 3, 2012.

(52) U.S. Cl.
CPC .......................... *A61N 2005/0627* (2013.01); *A61N 2005/064* (2013.01); *A61N 2005/0652* (2013.01); *A61N 2005/0654* (2013.01); *A61N 2005/0655* (2013.01); *A61N 2005/0661* (2013.01); *A61N 2005/0665* (2013.01); *A61N 2005/0667* (2013.01)

(56) References Cited

U.S. PATENT DOCUMENTS

| | | | |
|---|---|---|---|
| 5,576,591 A | 11/1996 | Werner | |
| 6,402,774 B1 | 6/2002 | Caldironi | |
| 6,413,268 B1 | 7/2002 | Hartman | |
| 6,436,127 B1 | 8/2002 | Anderson et al. | |
| 6,567,999 B1 | 5/2003 | Thurner | |
| 7,638,780 B2 | 12/2009 | Kilburn et al. | |
| 8,647,373 B1 | 2/2014 | Shepherd et al. | |
| 10,226,641 B2 * | 3/2019 | Moffat | A61N 5/0613 |
| 2001/0003800 A1 | 6/2001 | Crowley | |
| 2003/0045916 A1 | 3/2003 | Anderson et al. | |
| 2003/0100935 A1 | 5/2003 | Kratz | |
| 2004/0138726 A1 | 7/2004 | Savage | |
| 2004/0186082 A1 | 9/2004 | Hartman | |
| 2004/0225339 A1 | 11/2004 | Yaroslavsky et al. | |
| 2005/0015124 A1 | 1/2005 | Irwin | |
| 2005/0143793 A1 | 6/2005 | Korman et al. | |
| 2005/0148270 A1 | 7/2005 | Eden | |
| 2005/0261750 A1 | 11/2005 | McDaniel | |
| 2006/0106435 A1 | 5/2006 | Fraval | |
| 2006/0151709 A1 | 7/2006 | Hahl | |
| 2006/0206173 A1 | 9/2006 | Gertner et al. | |
| 2006/0217789 A1 | 9/2006 | Perez | |
| 2007/0208395 A1 | 9/2007 | Leclerc et al. | |
| 2007/0233210 A1 | 10/2007 | Morita et al. | |
| 2008/0103560 A1 | 5/2008 | Powell et al. | |
| 2008/0125834 A1 | 5/2008 | Hendrix et al. | |
| 2008/0172113 A1 | 7/2008 | Gourgouliatos et al. | |
| 2008/0211378 A1 | 9/2008 | Dutta et al. | |
| 2008/0224592 A1 | 9/2008 | Reich et al. | |
| 2008/0312721 A1 | 12/2008 | Lemieux | |
| 2009/0005839 A1 | 1/2009 | Griffith et al. | |
| 2009/0020711 A1 | 1/2009 | Hansmann et al. | |
| 2009/0093799 A1 | 4/2009 | Davenport et al. | |
| 2009/0118799 A1 | 5/2009 | Nanninga | |
| 2009/0134345 A1 | 5/2009 | Gentry et al. | |
| 2010/0185064 A1 | 7/2010 | Bandic et al. | |
| 2010/0241196 A1 | 9/2010 | Meyer | |
| 2010/0331929 A1 | 12/2010 | Burrows et al. | |
| 2011/0004280 A1 | 1/2011 | Irwin | |
| 2011/0212410 A1 | 9/2011 | Fiset | |
| 2011/0218595 A1 | 9/2011 | McMillan | |
| 2011/0299056 A1 | 12/2011 | Williamson et al. | |
| 2012/0071954 A1 | 3/2012 | Kao et al. | |
| 2012/0148976 A1 | 6/2012 | Brawn | |
| 2012/0282135 A1 | 11/2012 | Trapani | |
| 2013/0018442 A1 | 1/2013 | Irwin et al. | |
| 2013/0030264 A1 | 1/2013 | Gopalakrishnan et al. | |
| 2013/0131762 A1 | 5/2013 | Oversluizen | |
| 2013/0172963 A1 | 7/2013 | Moffat | |
| 2013/0245724 A1 | 9/2013 | Kaufman | |
| 2013/0253621 A1 | 9/2013 | DeLuca et al. | |
| 2013/0310730 A1 | 11/2013 | Goren et al. | |
| 2014/0074193 A1 | 3/2014 | Luzon | |
| 2014/0121732 A1 | 5/2014 | Goren et al. | |
| 2014/0276248 A1 | 9/2014 | Hall | |
| 2014/0277299 A1 | 9/2014 | Intintoli | |
| 2015/0088231 A1 | 3/2015 | Rubinfeld | |
| 2015/0102208 A1 | 4/2015 | Appelboom et al. |
| 2015/0165229 A1 | 6/2015 | Rodrigues |
| 2015/0217130 A1 | 8/2015 | Gross et al. |
| 2015/0217132 A1 | 8/2015 | Makkapati et al. |
| 2015/0238774 A1 | 8/2015 | Anderson et al. |
| 2016/0048826 A1 | 2/2016 | Fefferman |
| 2016/0129279 A1 | 5/2016 | Ferolito |
| 2016/0303395 A1 | 10/2016 | Moffat |
| 2016/0317686 A1 | 11/2016 | Dayton |
| 2017/0056238 A1 | 3/2017 | Yi et al. |
| 2017/0118854 A1 | 4/2017 | Dumon |
| 2017/0225006 A1 | 8/2017 | Anderson et al. |
| 2018/0014777 A1 | 1/2018 | Amir et al. |
| 2018/0056088 A1 | 3/2018 | Moffat |
| 2018/0133503 A1 | 5/2018 | Moffat |
| 2018/0206779 A1 | 7/2018 | Kono |
| 2018/0353770 A1 | 12/2018 | Moffat |
| 2018/0360709 A1 | 12/2018 | Rabe et al. |
| 2018/0369604 A1 | 12/2018 | Gamelin |
| 2019/0099613 A1 | 4/2019 | Estes et al. |
| 2019/0133515 A1 | 5/2019 | Park |
| 2019/0160303 A1 | 5/2019 | Moffat, IV |
| 2020/0030628 A1 | 1/2020 | Moffat et al. |
| 2020/0212265 A1 | 7/2020 | Ho et al. |
| 2020/0376292 A1 | 12/2020 | Moffat et al. |
| 2020/0391049 A1 | 12/2020 | Moffat et al. |
| 2021/0128939 A1 | 5/2021 | Verghese |
| 2022/0249863 A1 | 8/2022 | Moffat et al. |
| 2023/0347164 A1 | 11/2023 | Lauder et al. |

FOREIGN PATENT DOCUMENTS

| | | |
|---|---|---|
| CN | 201871131 | 6/2011 |
| CN | 104168953 | 7/2013 |
| CN | 107427688 | 8/2016 |
| CN | 106573155 | 4/2017 |
| DE | 7623367 | 2/1977 |
| DE | 3126236 | 1/1983 |
| DE | 9000705 | 3/1990 |
| DE | 19622074 | 12/1997 |
| DE | 20114790 | 12/2001 |
| DE | 10240716 | 3/2004 |
| DE | 202008004045 | 6/2008 |
| DE | 202008016045 | 4/2009 |
| EP | 0545887 | 6/1993 |
| EP | 1504792 | 2/2005 |
| EP | 1529552 | 5/2005 |
| EP | 1839703 | 10/2007 |
| EP | 1849497 | 10/2007 |
| EP | 1916017 | 4/2008 |
| EP | 2228098 | 9/2010 |
| GB | 2020970 | 11/1979 |
| JP | H05-220231 | 8/1993 |
| JP | 10-295837 | 10/1998 |
| JP | 3075306 | 11/2000 |
| JP | 2008-500846 | 10/2005 |
| JP | 2007267936 | 10/2007 |
| JP | 2008-73148 | 4/2008 |
| WO | WO9917668 | 4/1999 |
| WO | WO200002491 | 1/2000 |
| WO | WO2003047682 | 6/2003 |
| WO | WO2007001364 | 1/2007 |
| WO | WO2007106856 | 9/2007 |
| WO | WO2007143862 | 12/2007 |
| WO | WO2008027438 | 3/2008 |
| WO | WO2010016009 | 2/2010 |
| WO | WO2011097383 | 8/2011 |
| WO | WO2012142427 | 10/2012 |
| WO | WO2013103743 | 7/2013 |
| WO | WO2015061773 | 4/2015 |
| WO | WO2015130891 | 9/2015 |
| WO | WO2016007798 | 1/2016 |
| WO | WO2016127120 | 8/2016 |
| WO | WO2016154343 | 9/2016 |
| WO | WO2016176360 | 11/2016 |
| WO | WO2016203461 | 12/2016 |
| WO | WO2017136891 | 8/2017 |

(56) References Cited

FOREIGN PATENT DOCUMENTS

| WO | WO2018067411 | 4/2018 |
|---|---|---|
| WO | 2019118773 A1 | 6/2019 |
| WO | WO2019118777 | 6/2019 |

OTHER PUBLICATIONS

"Center Wavelength (CW) and Full Width at Half Maximum (GWHM) filter numbers," webpage at http://mdc.custhelp.com/app/answers/detail/a_id/19235/-/center-wavelength-%28cw%29-and-full-width-at-half-maximum-%28fwhm%29-filter-numbers, published Mar. 16, 2011, 1 page.
"Ergoline Vitamin D3 Solarium mit Dr. Holick UV-Systems," Sep. 2005, Ergoline GMBH Germany, Internet: www.ergoline. DE, 112 pages.
"Solaria Köln 2005," International Trade Fair for Sunlight Systems, Oct. 2005, English Google machine translation included, 9 pages.
Ala-Houhala, MJ., et al., "Comparison of narrow-band ultraviolet B exposures and oral vitamin D substitution on serum 25-hydroxyvitamin D concentration," Br J Dermatol. Apr. 2012. (5 pgs).
Australian Exam Report for co-pending Australian Application No. 2013206887, Applicant: BeneSol, Inc.; Date of Mailing: Feb. 24, 2017, 4 pages.
Bouillon, R., et al., "Action spectrum for production of previtamin D3 in human skin," CIE Technical Report 174, Commission International de l'Eclairage (CIE). 2006. (16 pgs).
Brozyna, et al., "Mechanism of UV-related carcinogenesis and its contribution to nevi/melanoma," Oct. 8, 2008, National Institute of Health Public Access, pp. 2 and 4.
Bruls, Wa., et al., "Transmission of UV-radiation through human epidermal layers as a factor influencing the minimal erythema dose," Photochemistry and Photobiology. Jan. 1984. (5 pgs).
Bunker, JWM., et al., "Precise evaluation of ultraviolet therapy in experimental rickets," New England Journal of Medicine. 1937. (6 pgs).
Changaris, DG., et al., "Pulsed UVB Irradiation Converts 7-dehydrocholesterol to previtamin D3 and Photoproducts," 2001. (10 pgs).
Chen, TC., et al., "Factors that influence the cutaneous synthesis and dietary sources of vitamin D," Archives of Biochemistry and Biophysics. Apr. 15, 2007. (4 pgs).
Clemens, TL., et al., "Increased skin pigment reduces the capacity of skin to synthesise vitamin D3," Lancet. Jan. 1982. (3 pgs).
De Fabo, EC., et al., "Mechanism of immune suppression by ultraviolet irradiation in vivo. I. Evidence for the existence of a unique photoreceptor in skin and its role in photoimmunology," The Journal of Experimental Medicine. Jul. 1983. (15 pgs).
Devgun, MS., et al., "Tanning, protection against sunburn and vitamin D formation with a UV-A 'sun-bed". The British Journal of Dermatology. Sep. 1982. (11 pgs).
Diffey, BL. "Observed and predicted minimal erythema doses: a comparative study," Photochemistry and Photobiology. Oct. 1994. (3 pgs).
Diffey, BL., et al., "A preliminary study on photoaddition and erythema due to UVB radiation," Physics in Medicine and Biology. Apr. 1984. (8 pgs).
English Translation of Chinese Office Action for Application No. 201480066635.X, Applicant: BeneSol, Inc., Date of Mailing: Nov. 7, 2017, 11 pages.
English translation of Chinese Office Action received for CN Application No. 201610833794.9, Applicant: BeneSol, Inc., Date of Mailing: Aug. 1, 2018, 13 pages.
English translation of Chinese Office Action received for CN Application No. 201680021252.X, Applicant: BeneSol, Inc., Date of Mailing: Jan. 18, 2019, 17 pages.
English translation of Chinese Office Action received for CN Application No. 201680037887.9, Applicant: BeneSol, Inc., Date of Mailing: Mar. 19, 2019, 19 pages.
English Translation of Japanese Office Action for Application No. 2014-550552, Applicant: BeneSol, Inc.; Date of Mailing: Oct. 4, 2016, 10 pages.
English Translation of Penultimate Japanese Office Action for Application No. 2017-074482, Applicant: BeneSol, Inc .; Date of Mailing: Oct. 29, 2018, 9 pages.
English Translation of Russian Office Action for Application No. 2014131906, Applicant: BeneSol, Inc.; Date of Mailing: Nov. 21, 2016, 10 pages.
English Translation of Second Japanese Office Action for Application No. 2014-550552, Applicant: BeneSol, Inc.; Date of Mailing: Jul. 28, 2017, 8 pages.
Examiner's Report for co-pending Canadian Patent Application No. 2,861,620, Applicant: BeneSol, Inc., Date of Mailing: Jul. 24, 2018, 4 pages.
Examiner's Requisition for Canadian Patent Application No. 2,861,620, Date of Mailing Nov. 5, 2021, 3 pages.
Extended European Search Report for European Patent Application No. 18888140.3, Date of Mailing Aug. 25, 2021, 8 pages.
Extended European Search Report for co-pending European Patent Application No. 17195774.9, Applicant: BeneSol, Inc., Date of Mailing: May 17, 2018, 9 pages.
Extended European Search Report for European Patent Application No. 18887658.5, mailing date Sep. 27, 2021, 8 pages.
Extended European Search Report for European Patent Application No. 16747382.6, Applicant: BeneSol, Inc., Date of Mailing: Oct. 1, 2018, 8 pages.
Extended European Search Report for European Patent Application No. 16787092.2, Applicant: BeneSol, Inc., Date of Mailing: Jan. 18, 2019, 9 pages.
Extended European Search Report in Application No. 13733883.6, Applicant: BeneSol, Inc., Date of Mailing: May 12, 2015, 7 pages.
Extended European Search Report received for European Patent Application No. 17858943.8, Applicant: BeneSol, Inc., Date of Mailing: May 12, 2020, 9 pages.
Extended European Search Report received for European Patent Application No. 20183232.6, Applicant: BeneSol, Inc., Date of Mailing: Nov. 24, 2020, 8 pages.
Farr, PM., et al., "The erythemal response of human skin to ultraviolet radiation," The British Journal of Dermatology. Jul. 1985. (13 pgs).
First European Examination Report in Application No. 13733883.6, Applicant: BeneSol, Inc., Date of Mailing: Sep. 1, 2016, 4 pages.
First Examination Report for co-pending Australian Patent Application No. 2018200369, Applicant: BeneSol, Inc., Date of Mailing: Jun. 22, 2018, 2 pages.
Fitzpatrick, "The validity and practicality of sun-reactive skin types I through VI," Arch Dermatol. Jun. 1988, 124(6):869-71, 3 pages.
Galkin, ON., et al., "'Vitamin D' viodosimeter: basic characteristics and potential applications," Journal of Photochemistry and Photobiology. Nov. 1999. (8 pgs).
Guilhou, JJ., et al., "Vtiman D metabolism in psoriasis before and after phototherapy," Acta Derm Venereol. 1990. (5 pgs).
Haddad, JG., et al., "Human plasma transport of vitamin D after its endogenous synthesis," J Clin Invest. Jun. 1993. (4 pgs).
Holick, MF. "Environmental factors that influence the cutaneous production of vitamin D," Am J Clin Nutr. Mar. 1995. (8 pgs).
Holick, MF. "Sunlight, UV-radiation, vitamin D and skin cancer: how much sunlight do we need?" Advances in Experimental Medicine and Biology. 2008. (15 pgs).
Holick, MF., et al., "Skin as the site of vitamin D synthesis and target tissue for 1,25-dihydroxyvitamin D3. Use of calcitriol (1,25-dihydroxyvitamin D3) for treatment of psoriasis," Archives of Dermatology. Dec. 1987. (14 pgs).
Holick, MF., et al., "Photosynthesis of previtamin D3 in human skin and the physiologic consequences," Science. Oct. 1980. (3 pgs).
Holick, MF., et al., "Regulation of cutaneous previtamin D3 photosynthesis in man: skin pigment is not an essential regulator," Science. Feb. 1981. (4 pgs).
Holick, MF., et al., "The photoproduction of 1 alpha, 25-dihydroxyvitamin D3 in skin: an approach to the therapy of vitamin-D-resistant syndromes," The New England Journal of Medicine. Aug. 1980. (6 pgs).

(56) References Cited

OTHER PUBLICATIONS

Holick, MF., et al., "Vitamin D and skin physiology: a D-lightful story," Journal of Bone and Mineral Research. Dec. 22, 2007.1_6 pgs).
Hume, EM., et al., "On the Absorption of Vitamin D from the Skin," *The Biochemical Journal*. 1927. (6 pgs).
International Search Report and Written Opinion for International Application No. PCT/US2013/020179 filed Jan. 3, 2013, Applicant: BeneSol, Date of Mailing: Apr. 25, 2013, 13 pages.
International Search Report and Written Opinion for International Application No. PCT/US2014/062352 filed Oct. 27, 2014, Applicant: BeneSol, Inc., Date of Mailing: Feb. 5, 2015, 12 pages.
International Search Report and Written Opinion for International Application No. PCT/US2016/016873 filed Feb. 5, 2016, Applicant: BeneSol, Inc., Date of Mailing: May 5, 2016, 12 pages.
International Search Report and Written Opinion for International Application No. PCT/US2016/029615 filed Apr. 27, 2016, Applicant: BeneSol, Inc., Date of Mailing: Oct. 7, 2016, 14 pages.
International Search Report and Written Opinion for International Application No. PCT/US2018/065537 filed Dec. 13, 2018, Applicant: BeneSol, Inc., Date of Mailing: Mar. 1, 2019, 10 pages.
International Search Report and Written Opinion for International Application No. PCT/US2018/065542 filed Dec. 13, 2018, Applicant: BeneSol, Inc., Date of Mailing: Mar. 26, 2019, 8 pages.
Jablonski, Ng., et al., "The evolution of human skin coloration," *Journal of Human Evolution*. Jul. 2000. (50 pgs).
English Translation of Japanese Office Action for Application No. 2016-550685, Applicant: BeneSol, Inc.; Date of Mailing Aug. 23, 2018, 4 pages.
Knudson, A., et al., "Quantitative studies of the effectiveness of ultraviolet radiation of various wave-lengths in rickets," *Journal Biological Chemistry*. 1938. (13 pgs).
Krause, R., et al., "UV radiation and cancer prevention: what is the evidence?" *Anticancer Research*. Jul. 2006. (5 pgs).
Lehmann, B., "The vitamin D3 pathway in human skin and its role for regulation of biological processes," *Photochemistry and Photobiology*. 2005. (6 pgs).
Lehmann, B., et al., "A novel pathway for hormonally active calcitriol," *Hormone Research*. 2000. (4 pgs).
Lehmann, B., et al., "Demonstration of UVB-induced synthesis of 1 alpha, 25-dihydroxyvitamin D3 (calcitriol) in human skin by microdialysis," *Archives of Dermatological Research*. Apr. 2003. (5 pgs).
Lehmann, B., et al., "Rold for tumor necrosis factor-alpha in UVB-induced conversion of 7-dehydrocholesterol to 1alpha,25-dihydroxyvitamin D3 in cultured keratinocytes," *The Journal of Steroid Biochemistry and Molecular Biology*. May 2004. (5 pgs).
Lehmann, B., et al., "The UVB-induced synthesis of vitamin D3 and 1alpha, 25-dihydroxyvitamin D3 (calcitriol) in organotypic cultures of keratinocytes: effectiveness of the narrowband Philips TL-01 lamp (311 nm)." *J Steroid Biochem Mol Biol*. Mar. 2007. (4 pgs).
Lehmann, B., et al., "UVB-induced conversion of 7-dehydrocholesterol to 1 alpha,25-dihydroxyvitamin D3 (calcitriol) in the human keratinocyte line HaCaT," *Photochemistry and Photobiology*. Dec. 2000. (10 pgs).
Lehmann, B., et al., "UVB-induced conversion of 7-dehydrocholesterol to 1alpha,25-dihydroxyvitamin D3 in an in vitro human skin equivalent model," *The Journal of Investigative Dermatology*. Nov. 2001. (7 pgs).
Lesiak, A., et al., "Vitamin D serum level changes in psoriatic patients treated with narrowband ultra violet B phototherapy are related to the season of the irradiation," *Photodermatol Photoimmunol Photomed*. Dec. 2011. (7 pgs).
Liu, W., et al., "Skin phototyping in a Chinese female population: analysis of four hundred and four cases from four major cities of China," *Photodermatology, Photoimmuniology and Photomedicine*. Aug. 2006. (5 pgs).
MacLaughlin, JA., et al., "Spectral character of sunlight modulates photosynthesis of previtamin D3 and its photoisomers in human skin," *Science*. May 1982. (3 pgs).

Marcus, M., "Make Your Day Better With D," *USA Weekend*. Nov. 2011. (3 pgs).
Maughan, G.H. "Ultra-violet wavelengths valuable in the cure of rickets in chickens," *American Journal of Physiology*. 1928. (18 pgs).
McLoone, P., et al., "An action spectrum for the production of cis-urocanic acid in human skin in vivo," *The Journal of Investigative Dermatology*. May 2005. (4 pgs).
Mead, MN. "Benefits of sunlight: a bright spot for human health," *Environmental Health Perspectives*. Apr. 2008. (13 pgs).
Moan, J., et al., "Sunbeds as vitamin D Sources." *Photochemistry and Photobiology*. Nov. 2009. (8 pgs).
Nemanic, MK., et al., "In vitro synthesis of vitamin D-3 by cultured human keratinocytes and fibroblasts: action spectrum and effect of AY-9944," *Biochimica et Biophysica Acta*. Sep. 1985. (11 pgs).
Norval, M et al., "Is the action spectrum for the UV-induced production of previtamin D3 in human skin correct?" *Photochemical & Photobiological Sciences*. Jan. 2010. (7 pgs).
Notice of Opposition filed for co-pending European Patent Application No. 13733883.6, issued as 2800605, Applicant: BeneSol, Inc., Date of Mailing: Jul. 31, 2018, 33 pages.
Obi-Tabot, ET., et al., "A human skin equivalent model that mimics the photoproduction of vitamin D3 in human skin," *In Vitro Cellular & Developmental Biology*. Mar. 2000. (6 pgs).
Olds, WJ., et al., "In vitro model of vitamin D3 (cholecalciferol) synthesis by UV radiation: dose-response relationships," *Journal of Photochemistry and Photobiology*. Nov. 2008. (6 pgs).
Osmancevic, A., et al., "UVB therapy increases 25(OH) vitamin D syntheses in postmenopausal women with psoriasis," *Photodermatol Photoimmunol Photomed*. Oct. 2007. (7 pgs).
Osmancevic, A., et al., "Vitamin D production in psoriasis patients increases less with narrowband thatn with broadband ultraviolet B phototherapy." *Photodermatol Photoimmunol Photomed*. Jun. 2009. (5 pgs).
Osmancevic, A., et al., "Vitamin D status in psoriasis patients during different treatments with phototherapy," *J Photochem Photobiol B*. Nov. 2010. (7 pgs).
Parrish, JA., et al., "Action spectrum for phototherapy of psoriasis," *The Journal of investigative Dermatology*. May 1981. (5 pgs).
Partial Supplementary European Search Report for co-pending European Patent Application No. 14856603.7, Applicant: BeneSol, Inc., Mailed Apr. 13, 2017, 7 pages.
Porojnicu, AC., et al., "Sun beds and cod liver oil as vitamin D sources," *Journal of Photochemistry and Photobiology*. May 2008. (7 pgs).
Ryan, C., et al., "The effect of narrowband UV-B treatment for psoriasis on vitamin D status during wintertime in Ireland," *Arch Dermatol*. Aug. 2010. (8 pgs).
Sage, RJ., et al., "UV-based therapy and vitamin D," *Dermatologic Therapy*. Jan. 2010. (10 pgs).
Scientific Committee On Consumer Products, "Opinion on Biological effects of ultraviolet radiation relevant to health with particular reference to sunbeds for cosmetic purposes," *European Commission Health & Consumer Protection Directorate-General*. 8th plenary of the SCCP on Jun. 20, 2006. (43 pgs).
Stamp, TC., et al., "Comparison of oral 25-hydroxycholecalciferol, vitamin D, and ultraviolet light as determinants of circulating 25-hydroxyvitamin D," *Lancet*. Jun. 25, 1977. (3 pgs).
Suh, KS., et al., "Long-term evaluation of erythema and pigmentation induced by ultraviolet radiations of different wavelengths," *Skin Research and Technology*. May 2007. (8 pgs).
Tangpricha, V., et al., "Tanning is associated with optimal vitamin D status (serum 25-hydroxyvitamn D concentration) and higher bone mineral density." *The American Journal of Clinical Nutrition*. Dec. 2004. (5 pgs).
Terenetskaya, I. "Two methods for direct assessment of the Vitamin D synthetic capacity of sunlight and artificial UV sources," *The Journal of Steroid Biochemistry and Molecular Biology*. May 2004. (4 pgs).
Vahavihu, K., et al. "Heliotherapy improves vitamin D balance and atopic dermatitis," *The British Journal of Dermatology*. Jun. 2008. (6 pgs).

(56) References Cited

OTHER PUBLICATIONS

Vantieghem, K., et al., "UVB-induced production of 1,25-dihydroxyvitamin D3 and vitamin D activity in human keratinocytes pretreated with a sterol delta7-reductase inhibitor," *J Cell Biochem.* May 2006. (12 pgs).
Walterscheid, JP., et al., "Cis-urocanic acid, a sunlight-induced immunosuppressive factor, activates immune suppression via the 5-HT2A receptor," *Proc. Natl. Acad. Sci. U.S.A.* Nov. 2006. (6 pgs).
Webb, A.R., et al., "The role of sunlight in the Cutaneous production of vitamin D3," *Annual Review of Nutrition.* 1988. (6 pgs).
Webb, AR., et al., "Sunlight regulates the cutaneous production of vitamin D3 by causing its photodegradation," *The Journal of Clinical Endocrinology and Metabolism.* May 1989. (6 pgs).
Weinstock, MA. "Assessment of sun sensitivity by questionnaire: validity of items and formulation of a prediction rule," *Journal of Clinical Epidemiology.* Aug. 2006. (6 pgs).
Whitmore, SE., et al., "Tanning salon exposure and molecular alterations," *Journal of the American Academy of Dermatology.* May 2001. (6 pgs).
Wolff Tanning Systems Website, Retrieved Mar. 21, 2012. (3 pgs).
Youn, JI., et al., "Assessment of the usefulness of skin phototype and skin color as the parameter of cutaneous narrow band UVB sensitivity in psoriasis patients," *Photodermatology, Photoimmunology and Photomedicine.* Oct. 2003. (4 pgs).
Yuen, AW., et al., "Vitamin D: in the evolution of human skin colour," *Medical Hypothesis.* Jan. 2010. (6 pgs).
Extended European Search Report received for European Patent Application No. 21192571.4, Applicant: BeneSol, Inc., Date of Mailing: Feb. 3, 2022, 10 pages.
International Search Report and Written Opinion mailed Feb. 3, 2022 in International Patent Application No. PCT/US21/46578, 17 pages.
International Search Report and Written Opinion mailed Jan. 19, 2018 in International Patent Application No. PCT/US17/54578, 15 pages.
Examiner's Report for Canadian Patent Application No. 2,861,620, Applicant: BeneSol, Inc., Date of Mailing: Jun. 14, 2023, 3 pages.
Examination Report mailed Jan. 10, 2024 for European Patent Application No. 18888140.3, 4 pages.
Examiner's Report for Canadian Patent Application No. 2,861,620, Applicant: BeneSol, Inc., Date of Mailing: Mar. 8, 2024, 4 pages.
Examiner's Report for Canadian Patent Application No. 3,036,581, Applicant: BeneSol, Inc., Date of Mailing: Feb. 29, 2024, 4 pages.
Extended European Search Report mailed Jul. 23, 2024 for European Patent Application No. 21859096.6, 8 pages.

\* cited by examiner

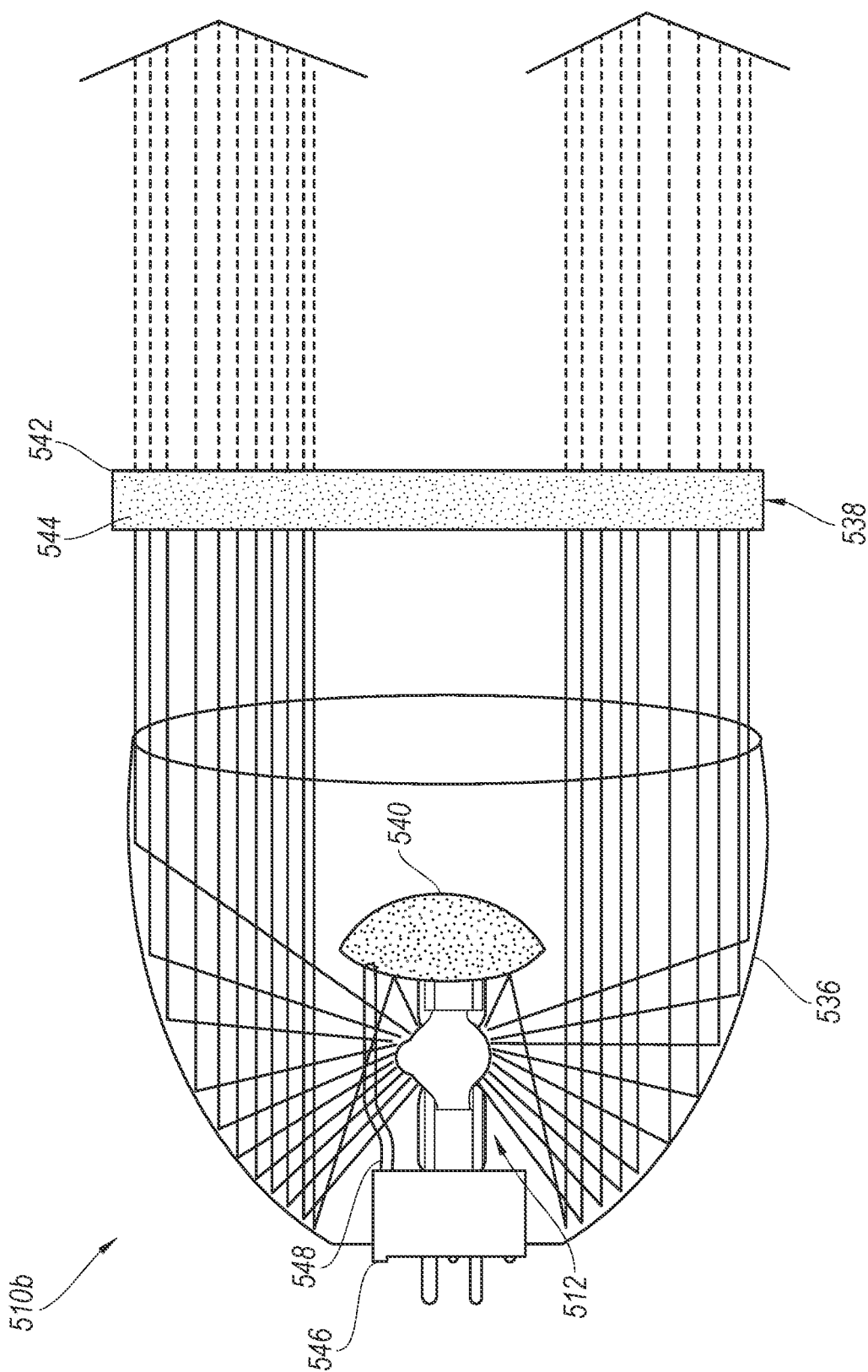

PHOTOTHERAPEUTIC APPARATUS FOR FOCUSED UVB RADIATION AND VITAMIN D SYNTHESIS AND ASSOCIATED SYSTEMS AND METHODS

CROSS-REFERENCE TO RELATED APPLICATION

This application is a continuation of U.S. patent application Ser. No. 16/262,682, filed Jan. 30, 2019, titled "PHOTOTHERAPEUTIC APPARATUS FOR FOCUSED UVB RADIATION AND VITAMIN D SYNTHESIS AND ASSOCIATED SYSTEMS AND METHODS," which is a divisional of U.S. patent application Ser. No. 13/733,860, filed Jan. 3, 2013, now issued as U.S. Pat. No. 10,226,641, titled "PHOTOTHERAPEUTIC APPARATUS FOR FOCUSED UVB RADIATION AND VITAMIN D SYNTHESIS AND ASSOCIATED SYSTEMS AND METHODS," which claims the benefit of and priority to U.S. Provisional Patent Application No. 61/582,778, filed Jan. 3, 2012, titled "PHOTOTHERAPEUTIC APPARATUS FOR FOCUSED UVB RADIATION AND VITAMIN D SYNTHESIS AND ASSOCIATED SYSTEMS AND METHODS," the contents of which are hereby incorporated by reference in their entireties.

TECHNICAL FIELD

The present technology relates to vitamin D phototherapy, and more particularly to phototherapeutic apparatuses for focused UVB radiation and vitamin D synthesis and associated systems and methods.

BACKGROUND

Vitamin D refers to a group of fat-soluble secosteriods that the human body can synthesize through adequate exposure to sunlight. More specifically, vitamin $D_3$ is made in the skin when 7-dehydrocholesterol reacts with ultraviolet B ("UVB") light. Vitamin D can also be absorbed from the various dietary sources, such as fatty fish (e.g., salmon and tuna), vitamin D fortified foods (e.g., dairy and juice products), and vitamin D supplements. Once absorbed, the vitamin D travels through the bloodstream to the liver where it is converted into the prohormone calcidiol. The calcidiol is, in turn, converted into calcitriol (the hormonally active form of vitamin D) by the kidneys or monocyte-macrophages in the immune system. When synthesized by the monocyte-macrophages, calcitriol acts locally as a cytokine to defend the body against microbial invaders. Kidney-synthesized calcitriol circulates through the body to regulate the concentration of calcium and phosphate in the bloodstream, and thereby promotes adequate mineralization, growth, and reconstruction of the bones. Therefore, an inadequate level of vitamin D, (typically characterized by a calcidiol concentration in the blood of less than 20-40 ng/m$^2$) can cause various bone softening diseases, such as rickets in children and osteomalacia in adults. Vitamin D deficiency has also been linked to numerous other diseases and disorders, such as depression, heart disease, gout, autoimmune disorders, and a variety of different cancers.

Recently, vitamin D deficiency has become a prominent condition due, at least in part, to increasingly metropolitan populations and the resultant indoor lifestyles that inhibit adequate daily exposure to sunlight for vitamin D production. The growing emphasis on skin cancer awareness and sunscreen protection, which blocks UVB rays, may have also increased the spread of vitamin D deficiency. Additionally, various environmental factors, such as geographic latitude, seasons, and smog, further impede sufficient vitamin D production.

Physicians have recommended vitamin D supplements as a preventative measure to increase vitamin D levels. The American Institute of Medicine, for example, recommends a daily dietary vitamin D intake of 600 international units (IU) for those 1-70 years of age, and 800 IU for those 71 years of age and older. Other institutions have recommended both higher and lower daily vitamin D doses. The limitations on daily dosages also reflect an effort to prevent ingesting too much vitamin D, which can eventually become toxic. In contrast, the human physiology has adapted to significantly higher daily doses of vitamin D from sunlight (e.g., 4,000-20,000 IU/day or more). UVB radiation has been identified as a more desirable source of vitamin D because of the ease at which vitamin D is produced from exposure to sunlight and the body's natural ability to inhibit excessive vitamin D intake through the skin.

BRIEF DESCRIPTION OF THE DRAWINGS

Many aspects of the present disclosure can be better understood with reference to the following drawings. The components in the drawings are not necessarily to scale. Instead, emphasis is placed on illustrating the principles of the present disclosure.

FIG. 5C is an enlarged partially schematic side view of a focused UVB radiation assembly for the phototherapeutic apparatus of FIG. 5A configured in accordance with another embodiment of the present technology.

DETAILED DESCRIPTION

The present technology is directed to apparatuses, systems, and methods for providing focused UVB radiation for vitamin D synthesis. Specific details of several embodiments of the technology are described below with reference to FIGS. 1A-8. Although many of the embodiments are described below with respect to phototherapeutic systems, devices, and methods for promoting vitamin D production in the skin, other applications (e.g., phototherapeutic treatment of skin diseases) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-8.

Figure 1B:
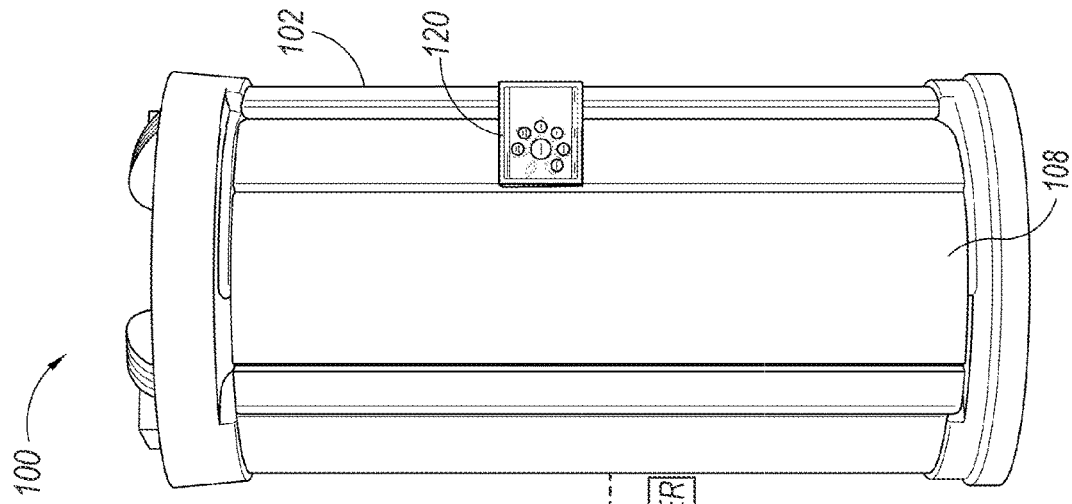
FIGS. 1A and 1B are isometric views of a phototherapeutic apparatus for focused UVB radiation in an open position and a closed position, respectively, configured in accordance with an embodiment of the present technology.
Figure 1A:
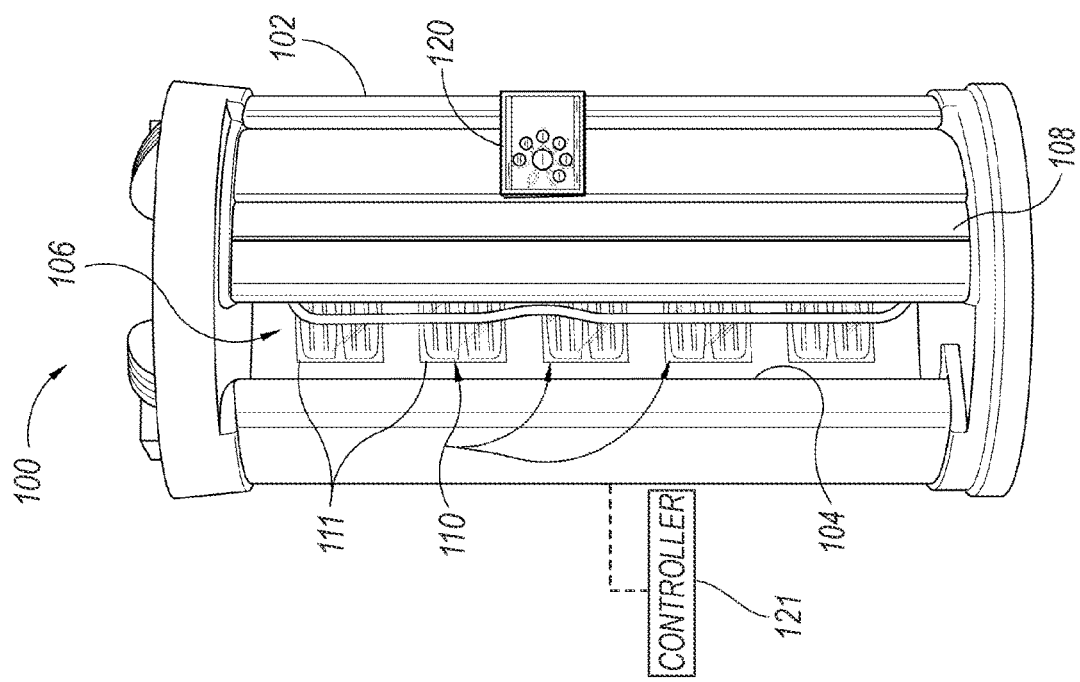
Figure 1C:
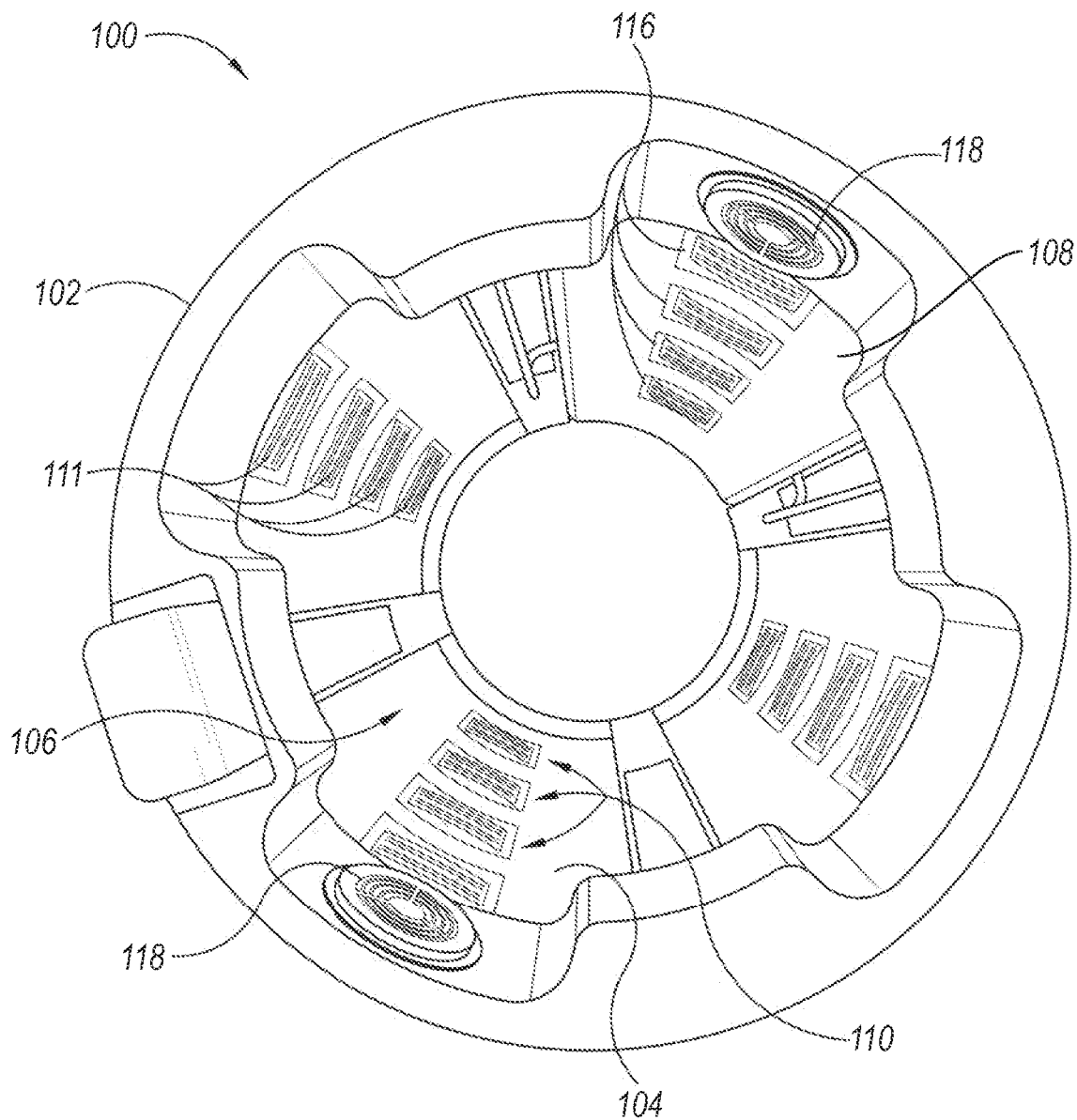
FIG. 1C is a top view of the phototherapeutic apparatus of FIGS. 1A and 1B.

FIGS. 1A and 1B are isometric views of a phototherapeutic apparatus 100 ("apparatus 100") for focused UVB radiation in an open position and a closed position, respectively, in accordance with an embodiment of the present technology, and FIG. 1C is a top view of the apparatus 100 of FIGS. 1A and 1B. Referring to FIGS. 1A-1C together, the apparatus 100 can include a housing 102 having one or more sidewalls 104 and a door 108 that define a chamber or interior space 106 configured to accommodate a user (e.g., a human patient). The housing 102 can carry a plurality of focused UVB radiation assemblies 110 that direct focused UVB radiation generally toward the interior space 106 or an irradiation zone in which the user can be exposed to focused UVB radiation. The focused UVB radiation assemblies 110 can generate UVB radiation within a predetermined spectrum to promote vitamin D production in human skin. For example, the predetermined spectrum can have a bandwidth of about 8 nm focused at about 297 nm (i.e., about 293-301 nm), which is generally considered the peak wavelength for vitamin D synthesis. In other embodiments, the predetermined spectrum of radiation can have a wider or narrower bandwidth (e.g., about 6-10 nm) and can be focused around other wavelengths (e.g., 296 nm, 300 nm, 302 nm, etc.) suitable for vitamin D production. The concentrated UVB radiation provided by the apparatus 100 can deliver a large dose of vitamin D (e.g., a weekly dose, a monthly dose, etc.) to the user within a relatively short phototherapy session (e.g., less than 10 minutes, less than 5 minutes, less than 2 minutes, less than 1 minute, etc.) in comparison to the length of sun exposure necessary to produce the same amount of vitamin D. In other embodiments, the focused UVB radiation assemblies 110 can be focused around other UVB wavelengths that provide therapeutic effects for skin diseases (e.g., psoriasis) or other disorders (e.g., eczema).

The housing 102 can be sized to allow users (e.g., adult humans) to stand completely within the interior space 106 during a phototherapy session. For example, the user can pivot, slide, and/or otherwise open the door 108 (e.g., as shown in FIG. 1A) to enter the interior space 106 and close the door 108 (e.g., as shown in FIG. 1B) to at least partially enclose the user within the housing 102. In various embodiments, the housing 102 can have a height of approximately 90-100 inches (228.6-254 cm) and an outer diameter of approximately 40-50 inches (101.6-127 cm), such as the Maxter V19 ER vertical tanning beds available from ISO Italia USA of Cleveland, Ohio. In other embodiments, the housing 102 can have other suitable dimensions and/or orientations to accommodate users within the interior space 106. For example, the housing 102 can be configured horizontally to allow the user to lie down during the phototherapy session. The full-body enclosure provided by the housing 102 can expose a large portion of the user's skin to the focused UVB radiation generated in the interior space 106, and therefore promote a substantial amount of vitamin D production via the user's skin during the phototherapy session. In other embodiments, the housing 102 can be smaller and/or configured to accommodate only a portion of the body, such as the face or upper body.

As shown in FIGS. 1A and 1C, a plurality of the focused UVB radiation assemblies 110 can be positioned on or in the sidewall 104 and/or the door 108 of the housing 102 behind protective covers or panels 111, and directed toward the interior space 106 such that the focused UVB radiation assemblies 110 at least partially surround the interior space 106. In the illustrated embodiment, the focused UVB radiation assemblies 110 are arranged in four columns around the perimeter of the interior space 106. In other embodiments, the focused UVB radiation assemblies 110 can be arranged in more or fewer columns, or otherwise positioned at least partially around the interior space 106.

As shown in FIG. 1C, the apparatus 100 can further include one or more cooling fans 118 or other cooling features directed generally toward the focused UVB radiation assemblies 110 and/or the interior space 106 of the housing 102 to at least reduce the operating temperature of the UVB radiation assemblies 110. The fans 118 can also be configured to cool the UVB radiation assemblies 110 before and/or after operation. In selected embodiments, the apparatus 100 can be configured to activate the fans 118 after the UVB radiation assemblies 110 have been turned on to allow the assemblies 110 to quickly ramp up to an operating temperature (e.g., a temperature that allows the UVB radiation assemblies 110 to generate UVB radiation) without interference from the fans 118. The duration of the delay between activation of the assemblies 110 and fan initiation can be, for example, less than a minute (e.g., 10-15 seconds, 3-5 seconds, etc.). The fan delay can decrease the overall phototherapy time (e.g., 30 seconds, 2 minutes, 5 minutes, etc.) by decreasing the time it takes for the UVB radiation assemblies 110 to begin producing focused UVB radiation. In other embodiments, the fans 118 can be set at a relatively low intensity and/or speed (e.g., as compared to typical tanning bed fans) to decrease the interference with the ramp up time of the UVB radiation assemblies 110. In further embodiments, the apparatus 100 can be configured to prevent the user from entering the interior space 106 until after the UVB radiation assemblies 110 are at or near their operating temperature such that the ramp up time does not increase the overall phototherapy time.

Figure 1D:
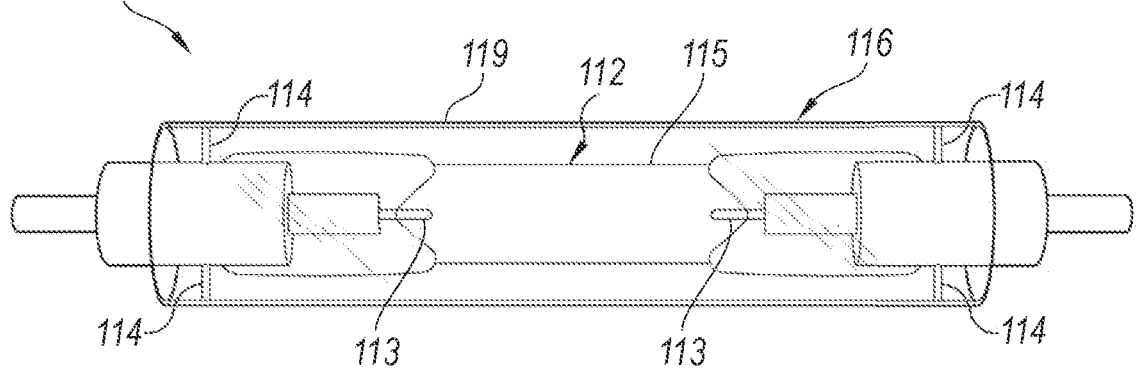
FIG. 1D is an enlarged side view of a focused UVB radiation assembly of the phototherapeutic apparatus of FIGS. 1A-1C configured in accordance with an embodiment of the present technology.

FIG. 1D is an enlarged side view of an individual focused UVB assembly 110 configured in accordance with an embodiment of the present technology. The focused UVB assembly 110 can include a UV radiation source 112 and a filter 116 on or over the UV radiation source 112 that at least substantially blocks UV radiation outside of a predetermined spectrum that facilitates vitamin D synthesis. In certain embodiments, for example, the filter 116 can substantially block UV radiation outside of a predetermined 10 nm spectrum ranging from approximately 292 nm to approximately 302 nm (i.e., centered at about 297 nm). In other embodiments, the filter 116 can be configured to block UV radiation outside of a predetermined spectrum having a wider or narrower bandwidth (e.g., a 5 nm spread, a 6 nm spread, an 8 nm spread, a 20 nm spread) and/or centered around a higher or lower wavelength (e.g., 296 nm, 300 nm, 302 nm, etc.).

In selected embodiments, the UV radiation source 112 includes one or more high intensity discharge ("HID") lamps, such as a metal-halide lamp that generates light by producing an electric arc through a gaseous mixture between electrodes 113 in an arc tube 115. As described in further detail below, in certain embodiments, the metal-halide radiation source 112 can be doped with chemicals to increase the UVB content of the energy emitted by the radiation source 112. In other embodiments, the UV radiation source 112 can include other types of HID lamps, lamps having higher or lower powered bulbs (e.g., 160 W, 200 W, 500 W, 650 W, 700 W, 800 W, etc.), and/or other suitable UV radiation sources. For example, the radiation source 112 can include a plurality of light emitting diodes (LEDs) that can emit light at one or more predetermined wavelengths (e.g., LEDs available from Sensor Electronic Technology, Inc. of Columbus, South Carolina), excimer lamps that can emit light within a narrow spectral range (e.g., excimer lamps available from Ushio of Cypress, Calif.), and/or pulsed xenon lamps (e.g., as described in further detail below with respect to FIG. 7).

In various embodiments, each of the UV radiation sources 112 may have the same intensity to provide substantially uniform UVB exposure to the user in the interior chamber 106. In other embodiments, the UV radiation sources 112 can be arranged according to varying degrees of power. For example, one or more UV radiation sources 112 with higher powered HID lamps (e.g., 650-800 W) can be positioned at an upper portion of the apparatus 100 (FIGS. 1A and 1C) proximate the facial region and one or more lower powered HID lamps (e.g., 500-600 W lamps) can be positioned at the lower portion of the apparatus 100. In other embodiments, the UV radiation sources 112 can be arranged in other suitable configurations to transmit UV radiation toward the interior space 106 of the apparatus 100.

In the embodiment illustrated in FIG. 1D, the filter 116 is a coated cylindrical tube or sleeve 119 that extends over the length (e.g., 4 inches) of the UV radiation source 112 and is offset from the UV radiation source 112 by a plurality of stand-offs 114 at each end portion of the filter 116. The stand-offs 114, for example, can create a 1 inch (25.4 mm) space between the UV radiation source 112 and the filter 116. The sleeve 119 may also provide an insulative enclosure over the UV radiation source 112 that allows the radiation source 112 to ramp up quickly to its operating temperature. In other embodiments, the stand-offs 114 can be longer or shorter, and/or the filter 116 can be separated from the UV radiation source 112 using other suitable means. In further embodiments, the filter 116 can have other suitable shapes that cover at least a portion of the UV radiation source 112.

The sleeve 119 can be made from a substrate (e.g., quartz glass, Plexiglas, etc.) coated with UV or other optical filtering materials, such as hafnium dioxide, zinc oxide, cesium, titanium dioxide, and/or various other optical filtering materials. One or more coatings can be applied to the substrate to filter out UV radiation below a lower threshold of the predetermined spectrum (e.g., wavelengths below 100 nm, 285 nm, 287 nm, 294 nm, etc.), and additional coatings can be applied to the substrate to filter out UV radiation above an upper threshold of the predetermined spectrum (e.g., wavelengths above 300 nm, 302 nm, 310 nm, etc.). For example, the filter 116 can include a titanium dioxide coating to block wavelengths less than 185 nm and prevent ozone from forming, and can include additional coatings to block other wavelengths outside the predetermined spectrum. In other embodiments, the substrate can include a single coating configured to at least substantially block UV radiation outside of the predetermined spectrum. In further embodiments, the substrate itself can serve as an absorption filter to block at least some energy with wavelengths below a predetermined spectrum, and an interference coating can be applied to the substrate to block energy with wavelengths higher than the predetermined spectrum.

The coating(s) can be applied to the sleeve 119 using chemical vapor deposition (CVD), physical vapor deposition (PVD), other deposition processes, and/or other suitable filter coating methods. In other embodiments, one or more coatings can be applied directly onto the UV radiation source 112 to block at least some of the UV radiation as it exits the source 112. In further embodiments, the filter coating(s) can be applied to other portions of the apparatus 100 between the UV radiation source 112 and the interior chamber 106 of the housing 102. For example, filter coating(s) can be applied to the protective covers 111 (FIGS. 1A and 1C) in front of the UVB radiation assemblies 110. In still further embodiments, the sleeve 119 and/or a portion of the UV radiation source 112 can be doped with filtering materials rather than coated.

In selected embodiments, the UV radiation source 112 can include a filament that generates radiation at least partially concentrated within the predetermined spectrum. For example, mercury-based lamps can have a relatively strong concentration of UVB radiation around 297 nm, and may therefore be used in conjunction with or in lieu of the filter 116 to transmit focused UVB radiation suitable for vitamin D synthesis. In other embodiments, the UV radiation source 112 can include other suitable filaments and/or features that reduce UV radiation outside of the predetermined spectrum.

Figure 2A:
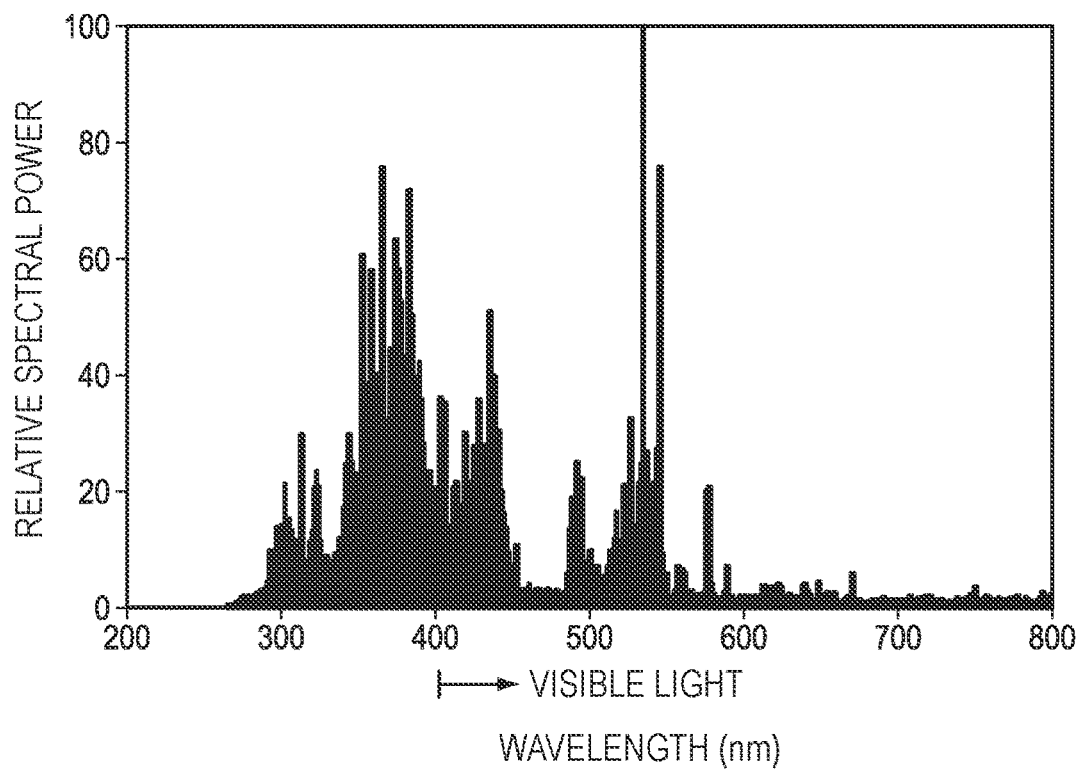
FIGS. 2A and 2B are exemplary graphical representations of relative spectral powers of a UV source before and after UVB filtering, respectively, in accordance with an embodiment of the present technology.
Figure 2B:
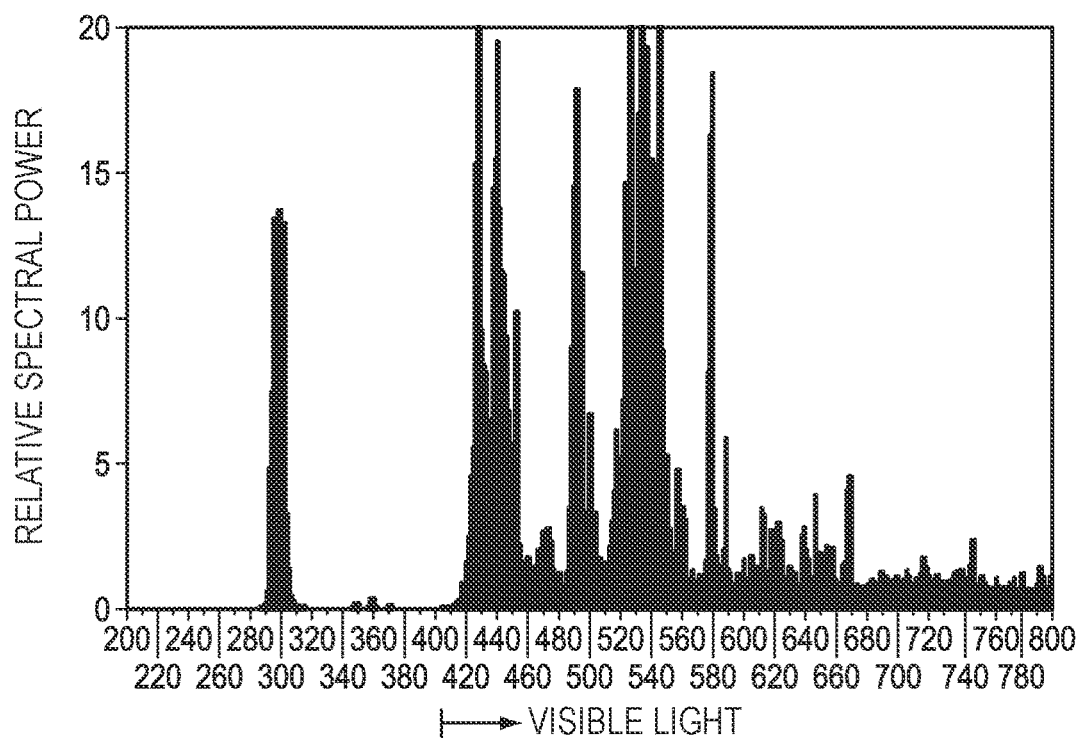

FIGS. 2A and 2B are exemplary graphical representations of the relative spectral powers of the UV radiation source 112 before and after focusing the UVB radiation with the filter 116. As shown in FIG. 2A, the UV radiation source 112 may generate UV light in a broad spectrum of wavelengths (e.g., between about 260-400 nm (i.e., visible light)). However, as shown in FIG. 2B, applying the filter 116 (e.g., the coated or doped sleeve 119, a coating on the UV radiation source 112, etc.) to the UV radiation source 112 can at least substantially block UV radiation less than approximately 290 nm and greater than approximately 310 nm. The filter 116 can, therefore, concentrate the UV radiation emitted by the UV radiation source 112 around the wavelengths associated with vitamin D production (e.g., 297 nm, 300 nm, 302 nm, etc.), and thereby provide sufficient UVB radiation to initiate high levels of vitamin D production (e.g., about 40,000 IU, about 70,000 IU, about 100,000 IU, etc.) within a relatively short period of time (e.g., less than 1 minute, less than 5 minutes, etc.).

During a phototherapy session, the apparatus 100 can expose the user to focused UVB radiation within a predetermined radiation spectrum to deliver a dose of vitamin D within a relatively short exposure time. In one embodiment, for example, the apparatus 100 can provide a dose of vitamin D in less than two minutes. The dose of vitamin D can be equivalent to the user's required weekly dose of vitamin D. For example, if the user requires a daily vitamin D dose of approximately 10,000 IU from sunlight, the apparatus 100 can deliver approximately 70,000 IU during the phototherapy session. In other embodiments, the apparatus 100 can be configured to provide larger or smaller daily vitamin D doses (e.g., 6,000 IU/day, 20,000 IU/day, etc.), and/or the vitamin D dose can correspond to vitamin D requirements for longer or shorter periods of time (e.g., a two day dose, a two week dose, a monthly dose, etc.).

The amount of vitamin D in the vitamin D dose can vary depending on user-specific characteristics, such as skin type (e.g., as determined by the Fitzpatrick scale or modifications thereof), age, weight, average sun exposure, and/or other parameters that may affect the vitamin D synthesis and needs. For example, users with lighter skin tones typically require a shorter UVB exposure times and/or lesser UVB intensities to receive a sufficient vitamin D dose than users with darker skin tones. Older users produce less vitamin D from the same amount of exposure to UVB as younger users, and therefore typically require longer exposure times and/or greater UVB intensity than younger users. The apparatus 100 can therefore be configured to provide varying levels of vitamin D by adjusting the duration of the phototherapy session and/or intensity of the focused UVB radiation. In other embodiments, the apparatus 100 does not adjust for user-specific characteristics, and performs a standardized phototherapy session on all users. Without being bound by theory, it is thought that the human body will inherently prevent toxic levels of vitamin D from being produced in the skin when the user is exposed to higher than necessary UVB radiation. Therefore, the apparatus 100 is at least less likely to produce toxic levels of vitamin D than vitamin D taken in the form of dietary supplements, which bypass the body's built-in protection.

The apparatus 100 can be adjusted for variations in the vitamin D dose using a local controller 121 (FIGS. 1A and 1B; shown schematically) and/or remote server coupled thereto via a communications link (e.g., the Internet, an intranet, etc.) based on various operational parameters. For example, the controller 121 can increase the vitamin D dose provided during a phototherapy session by increasing the length of the phototherapy session (i.e., the exposure time) because the user receives more UVB radiation during longer exposure times. The vitamin D dose can also be increased by increasing the concentration of filtered UVB rays associated with vitamin D synthesis (e.g., via the filter 116). In selected embodiments, the apparatus 100 can emit concentrated levels of UVB radiation that provide users with weekly doses of vitamin D within short exposure times, such as less than 5 minutes, 3 minutes, 2 minutes, 1 minute, 30 seconds, etc.

In various embodiments, the apparatus 100 can be configured to limit the vitamin D dose based on a minimum erythemal dose ("MED"), which is the threshold dose of UVB radiation that produces erythema (i.e., visible reddening of the skin 24 hours after exposure). The MED depends on the user's skin type, but the measurement has been standardized (using unprotected, untanned skin type 2 on the Fitzpatrick skin type scale) to compare and control UVB exposure in tanning beds. For example, certain regulations prohibit tanning beds from exceeding 4 standardized MEDs per exposure. As such, the apparatus 100 can also be configured to limit phototherapy sessions to 4 standardized MEDs. In other embodiments, the apparatus 100 can limit phototherapy sessions to less than 4 standardized MEDs, while still providing users with relatively high vitamin D doses because the narrow bandwidth of radiation generated by the UVB radiation assemblies 110 limit the user's UVB exposure to the focused spectrum of UVB radiation associated with vitamin D synthesis. In one embodiment, for example, the apparatus 100 can limit phototherapy sessions to approximately 1 standardized MED. In other embodiments, the apparatus 100 can adjust the phototherapy session based on the MED associated with the user's skin type (e.g., 75% of the user's MED, 50% of the user's MED, etc.). Accordingly, the apparatus 100 can at least reduce the likelihood of skin redness resulting from UVB exposure, while still providing sufficient levels of focused UVB radiation to induce vitamin D production during the phototherapy session. Therefore, the apparatus 100 can be configured to inhibit the negative effects (e.g., sunburn and skin cancer) typically associated with tanning beds and/or excessive sun exposure.

As further shown in FIGS. 1A and 1B, the apparatus 100 can also include a user interface 120 that allows the apparatus 100 to operationally interface with individuals receiving phototherapy (e.g., the users) and/or individuals administering the phototherapy (e.g., physicians or trained technicians) via visual and/or audible signals (e.g., textual instructions, audible commands, animations, etc.). For example, the user interface 120 can include a touch screen, display screen, keyboard, mouse, card swipe, PIN pad, and/or other suitable devices that can receive information and/or otherwise communicate with users. In the illustrated embodiment, the user interface 120 is positioned on the exterior of the housing 102. However, in other embodiments, the user interface 120 can be positioned elsewhere on the apparatus 100 (e.g., within the interior space 106), or can be remotely coupled to the apparatus 100 (e.g., via the Internet, a secured intranet, and/or other suitable connection).

The user interface 120 can provide instructions to the user related to the apparatus 100 and/or query the user regarding various user-specific characteristics that may affect the parameters of the UVB exposure provided by the apparatus 100. For example, the user interface 120 can instruct or prompt the user to answer questions related to his or her skin type (e.g., using a Fitzpatrick skin test and/or modifications thereof), and the apparatus 100 can use the answers to identify the user's skin type (e.g., via a controller or a remote computer communicatively coupled to the apparatus 100). The user interface 120 can also be configured to receive information related to the user's age, weight, recent sun exposure, diet, and/or other suitable factors that may affect the user's vitamin D needs. This user-specific information can be used to derive parameters for a phototherapy session, such as exposure time.

In selected embodiments, the user interface 120 can also be configured to receive feedback related to previous phototherapy sessions. For example, the user can indicate whether he or she experienced any redness caused by a previous phototherapy session (i.e., the phototherapy session exceeded the user's MED), and the apparatus 100 can adjust the parameters of subsequent phototherapy sessions to reduce or prevent future redness.

Figure 3A:
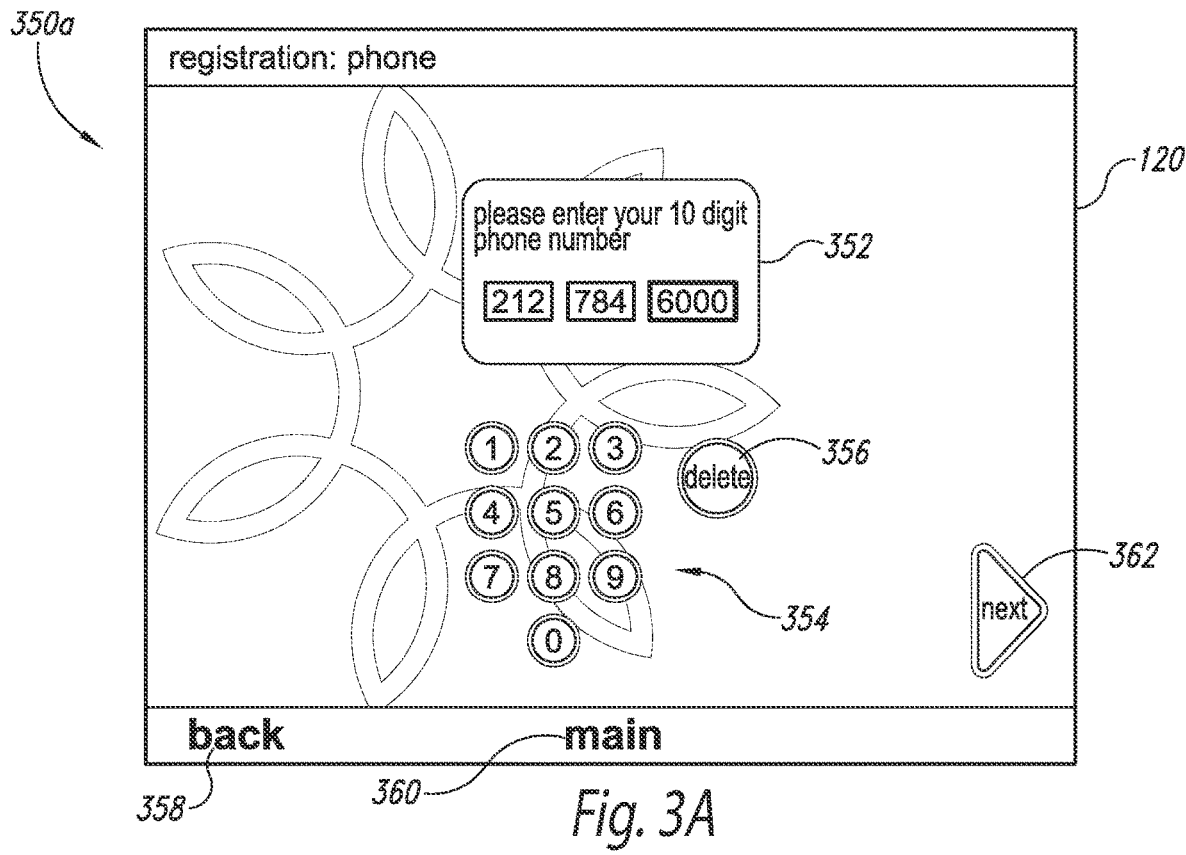
FIGS. 3A-3C illustrate display pages for a phototherapeutic apparatus for focused UVB radiation configured in accordance with an embodiment of the present technology.
Figure 3B:
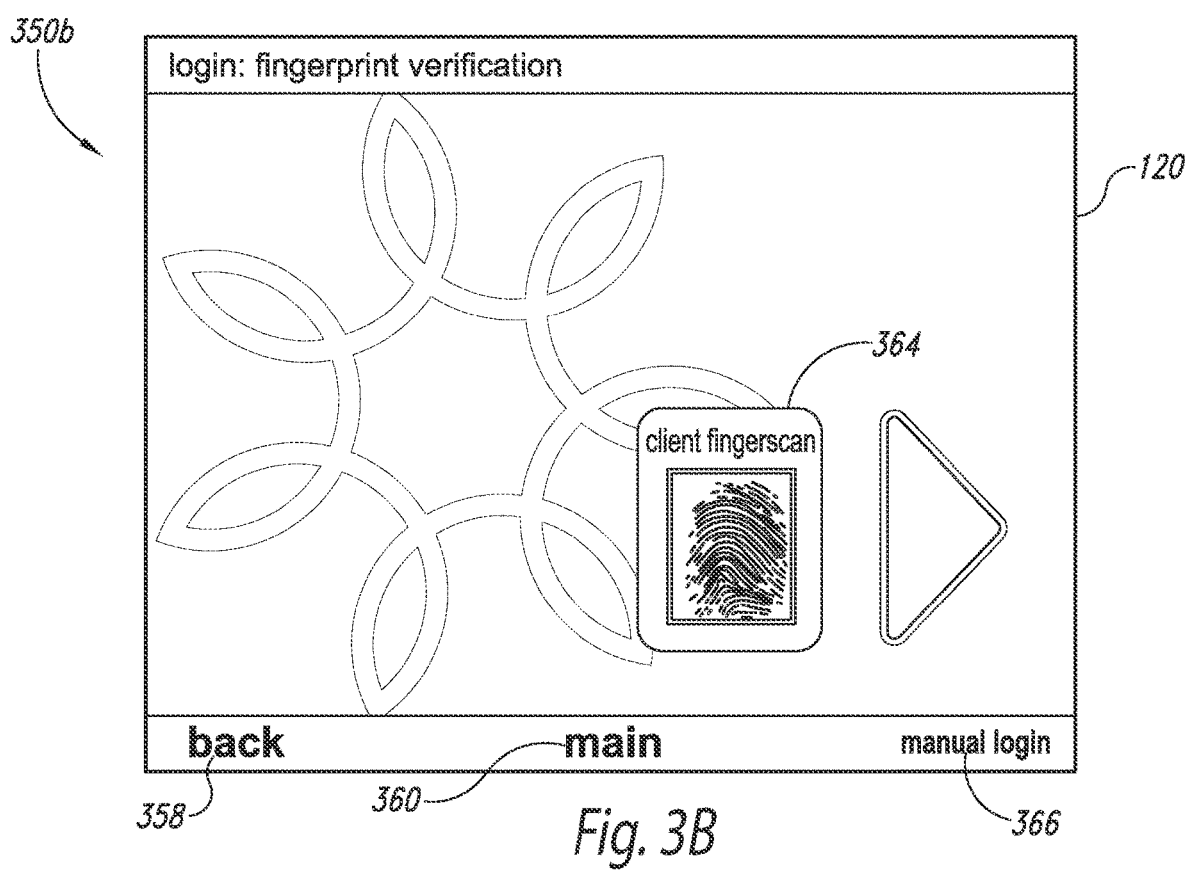
Figure 3C:
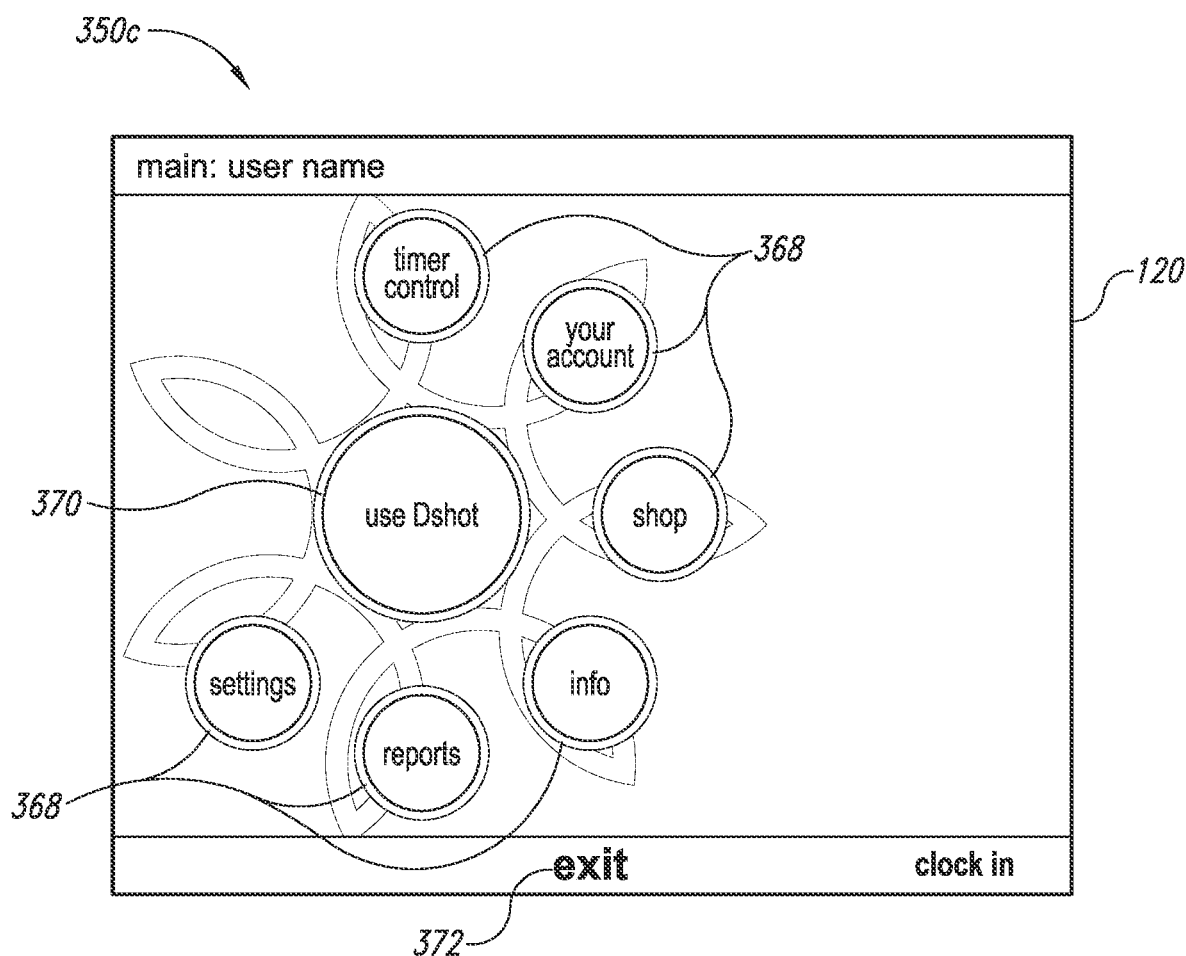

The user interface 120 can also be configured to create user accounts that associate users with phototherapy sessions performed by the apparatus 100 and/or other phototherapeutic apparatuses communicatively linked to the apparatus 100 in the same network. FIGS. 3A-3C, for example, illustrate display pages 350*a-c*, respectively, on the user interface 120 that can be used to register and log into a user account. In other embodiments, the display pages 350a-c can be displayed on other portions of the apparatus 100 (e.g., an additional display) and/or remote devices communicatively coupled thereto, such as a home computer or mobile phone communicatively coupled to the apparatus 100 via the Internet or other suitable communications link.

Referring first to FIG. 3A, the display page 350a can include various buttons or icons that allow the user to enter user identification information to register or create a user account. In the illustrated embodiment, the display page 350a includes a box 352 that requests the user to enter his or her phone number using a key pad 354 displayed on the display page 350a. The display page 350a also includes a "delete" button 356 to edit the numbers entered in the box 352 and buttons to navigate between display pages, such as a "back" button 358 to return to the previous page, a "main" button 360 to return to a home page, and/or other suitable buttons. In other embodiments, the display page 350a can be configured to receive other forms of user identification information to create the user account, including an email address and credit card information (e.g., entered via a card swipe).

Once the user has entered his or her identification information, the user can select a "next" button 362 to navigate to display page 350b illustrated in FIG. 3B. The display page 350b allows a user to log into his or her user account. A new user can scan his or her fingerprint via a fingerprint scan box 364 on the display page 364 during the initial registration phase, and the apparatus 100 can store this information locally or remotely on a database to allow the user to log into his or her user account during subsequent phototherapy sessions via fingerprint identification. In other embodiments, the fingerprint scan can be performed by a device positioned elsewhere on the apparatus 100. If the user does not wish to log in using his or her fingerprint, the user can select a "manual login" button 366 to manually access the user's account by typing in a user name, password, and/or other information that associates the user with his or her user account. In further embodiments, the user interface 120 can include facial recognition software that allows the apparatus 100 to recognize the user by scanning his or her face. This facial recognition scan may also be configured to allow the user interface 120 to determine the user's skin type and adjust the parameters of the phototherapy session accordingly. In still further embodiments, the user interface 120 and/or other portion of the apparatus 100 can include other suitable forms of biometric recognition to identify users.

Once the user has logged into his or her account, the user interface 120 can navigate to display page 350c shown in FIG. 3C that can serve as the user's home page. The display page 350c can include a plurality of selection buttons 368 that navigate the user interface 120 to various other display pages. For example, selecting a "timer control" button 368 can navigate the user interface 120 to a display page that allows the user to select or enter the duration of his or her phototherapy session. The user can select the "your account" button 368 to view and/or edit information related to his or her user account (e.g., the user's address, medical history, credit card associated with the user account, etc.), and the user can select the "settings" button 368 to navigate the user interface 120 to a display page where the user can view and/or edit settings associated with the apparatus 100, user preferences, and/or other user-specific settings (e.g., skin type, age, etc.). In various embodiments, the user can select the "settings" button 368 and/or other buttons on the display page 350c to enter feedback related to previous phototherapy sessions, and the apparatus 100 can modify subsequent phototherapy sessions accordingly. The "reports" button 368 can be selected to illustrate data related to the user's previous phototherapy sessions. For example, previous doses of vitamin D can be displayed for the user in the form of charts and/or graphs. The "reports" button 368 can also be configured to display other types of summaries related to the user and previous phototherapy sessions. In various embodiments, the user can select the "shop" button 368 to purchase a package of phototherapy sessions (e.g., on a per minute and/or per session basis) and/or related products. The "info" button 368 can be selected to show information related to the apparatus 100 in general (e.g., technical specifications), vitamin D-related information (e.g., daily dose recommendations, effects of vitamin D deficiency, articles related to vitamin D, etc.), and/or other suitable information. The "info" button can also be used to access online resources (e.g., medical journals) when the apparatus 100 is connected to the Internet and/or a secured intranet. When the apparatus 100 is connected to the Internet or an intranet, the selection buttons 368 can be used to access online resources (e.g., medical journals).

As further shown in FIG. 3C, the display page 350c can also include an activation button 370 (labeled "use Dshot") that allows the user to begin a phototherapy session. In various embodiments, the activation button 370 may navigate the display page 350c to a display that requests the user to add information that may affect the parameters of the phototherapy session. In another embodiment, the activation button 370 may begin a countdown to the beginning of the phototherapy session. This embodiment can accommodate for the ramp up time of the UVB radiation source 112 and/or other features of the apparatus 100. Additionally, as shown in FIG. 3C, the display page 350c can include an "exit" button 372 at any time to log out of his or her user account.

Figure 4:
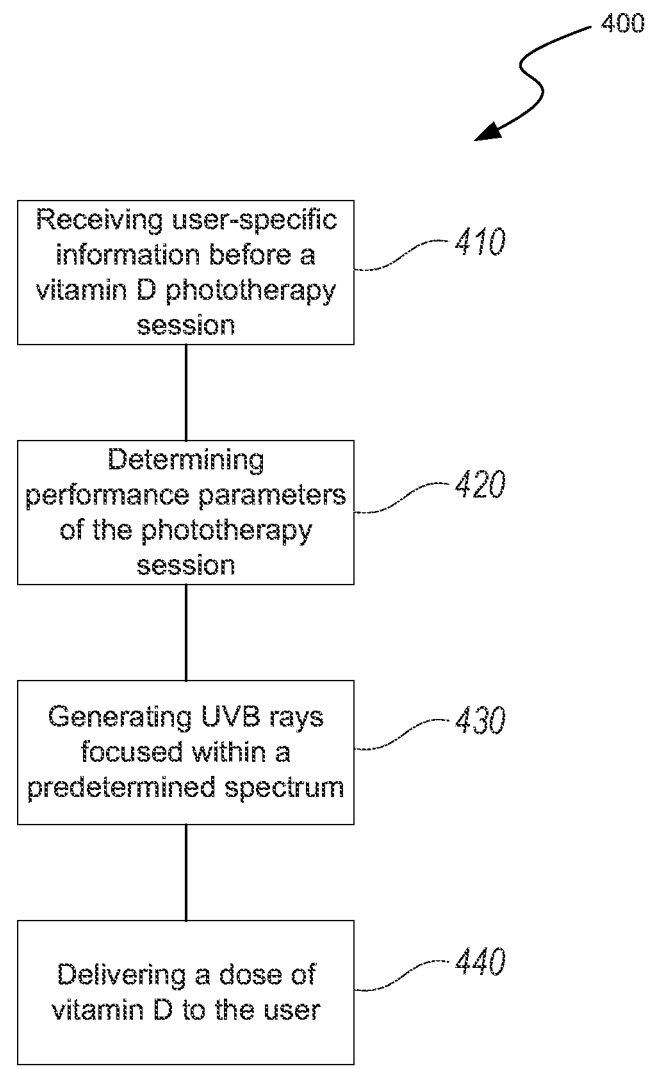
FIG. 4 is a block diagram illustrating a method of providing focused UVB radiation for vitamin D synthesis in accordance with an embodiment of the present technology.

FIG. 4 is a block diagram illustrating a method 400 of generating focused UVB radiation for vitamin D synthesis in accordance with an embodiment of the present technology. In various embodiments, the method 400 can be performed by a phototherapeutic apparatus including features generally similar to the features of the apparatus 100 described above with reference to FIGS. 1A-3C. The method 400 can optionally include receiving user-specific information before a vitamin D phototherapy session (block 410). The user-specific information may include skin type (e.g., as characterized by the Fitzpatrick scale), age, weight, current vitamin D level, feedback related to previous vitamin D phototherapy sessions, and/or other information that may affect the user's vitamin D dose and/or operating parameters of the phototherapeutic apparatus. In selected embodiments, the person undergoing the vitamin D phototherapy (i.e., the user) can enter his or her user-specific information via a user interface and/or other suitable device communicatively coupled to the phototherapeutic apparatus (e.g., via a website and/or a smart phone application). In other embodiments, the individual administering the phototherapy session (e.g., a physician, a nurse, etc.) can input the user-specific information via a user interface, a remote computer communicatively coupled to the phototherapeutic apparatus, and/or other suitable input devices. This embodiment allows the phototherapy to be controlled by a professional and avoids improper use by an untrained user.

The method 400 can continue by determining performance parameters of the phototherapy session via a local controller and/or a remote server coupled thereto (block 420). For example, an algorithm can use the user-specific information to determine the appropriate vitamin D dose provided by the apparatus, the duration of the phototherapy session, and/or the intensity of focused UVB exposure for the phototherapy session. In other embodiments, the user can select operational parameters of the phototherapy session (e.g., exposure time) without entering user-specific information, and/or override the recommended parameters provided by the algorithm. In further embodiments, the method can bypass block 420, and use non-user specific exposure parameters for the phototherapy session. In one embodiment, for example, each phototherapy session can deliver approximately 50,000 IU of vitamin D to a typical user within less than a minute of focused UVB exposure. In other embodiments, the parameters of the phototherapy session may differ.

As further shown in FIG. 4, the method 400 can include generating focused UVB rays within a predetermined spectrum (block 430). For example, a filter and/or a suitable UV radiation source can emit UVB radiation within a narrow bandwidth (e.g., a bandwidth of about 6-10 nm) generally centered at a wavelength (e.g., 297 nm, 302 nm, etc.) that facilitates efficient vitamin D production through the skin. In one embodiment, the predetermined spectrum ranges from approximately 290 nm to approximately 310 nm. In other embodiments, the predetermined spectrum can be broader or narrower.

Filtering and/or otherwise generating the focused UVB rays can deliver a dose of vitamin D to the user in a relatively short amount of time (block 440). For example, the method 400 can deliver a weekly dose of vitamin D (e.g., 700,000 IU) within 2 minutes. The vitamin D dose provided by the apparatus can be approximated by the previously provided user-specific characteristics and the operating parameters of the apparatus. To obtain different vitamin D doses, for example, the method 400 can include increasing the intensity of the UVB rays within the predetermined spectrum and/or focusing the predetermined spectrum more closely toward the wavelength associated with vitamin D synthesis. The exposure time can also be adjusted to change the vitamin D dose. In further embodiments, the method 400 can also include adjusting the parameters of the phototherapy session to limit the MED the user is exposed to and/or other suitable steps associated with providing vitamin D phototherapy.

Figure 5A:
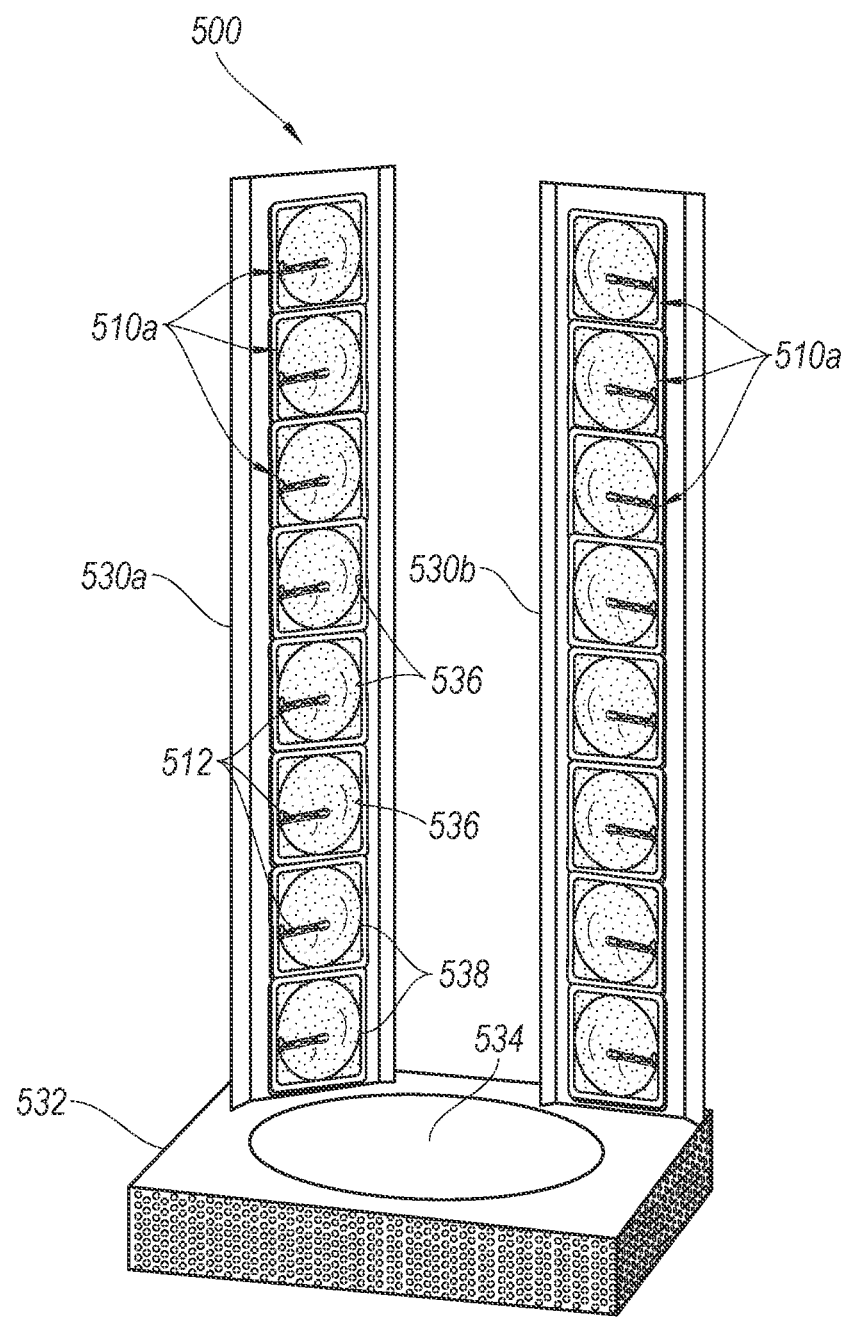
FIG. 5A is an isometric view of a phototherapeutic apparatus for focused UVB radiation configured in accordance with another embodiment of the present technology.

FIG. 5A is an isometric view of a phototherapeutic apparatus 500 ("apparatus 500") for focused UVB radiation configured in accordance with another embodiment of the present technology. The apparatus 500 includes several features generally similar to the features of the apparatus described above with respect to FIGS. 1A-1D. For example, the apparatus includes a plurality of focused UVB radiation fixtures or assemblies 510a ("radiation assemblies 510a") that emit energy within a predetermined wavelength spectrum (e.g., about 293-301 nm, 298-306 nm, etc.). In the illustrated embodiment, the radiation assemblies 510a are carried by two housings, arms or columns (identified individually as a first column 530a and a second column 530b, and referred to collectively as columns 530) that are mounted on or otherwise attached to a pedestal or base 532, and the radiation assemblies 510a are directed generally inward toward a central portion 534 of the base 532. The base 532 and the columns 530 together define an irradiation zone in which a human patient can be exposed to focused UVB energy emitted by the radiation assemblies 510a. When a user (e.g., a human patient) stands on or is otherwise positioned at the central portion 534 of the base 532, the radiation assemblies 510a can irradiate the user's skin to stimulate vitamin D production in the skin during a phototherapy session. In various embodiments, the central portion 534 of the base 532 and/or the columns 530 may rotate relative to each other (e.g., the columns 530 may rotate around the central portion 534) to expose all sides of the user's body to the energy emitted by the radiation assemblies 510a.

In the embodiment illustrated in FIG. 5A, the apparatus 500 includes eight radiation assemblies 510a in each column 530 that emit energy at substantially similar wavelengths and similar intensities. In certain embodiments, the radiation assemblies 510a in the first column 530a can be vertically offset from the radiation assemblies 510a in the second column 530b to prevent the irradiation from radiation assemblies 510a of the first column 530a from directly overlapping the irradiation from the radiation assemblies 510a of the second column 530b. For example, the radiation assemblies 510a in the first column 530a can be offset from radiation assemblies 510a in the second column 510ab by about one radius of an individual radiation assembly 510a. This staggering of the radiation assemblies 510a can provide a more uniform intensity of irradiation along the length of the columns 530 and prevent certain areas of a user's skin from being exposed to more irradiation than others. In other embodiments, the apparatus 500 can include columns 530 with fewer than or more than eight radiation assemblies 510a, a single column 530 of radiation assemblies 510a, more than two columns 530 of radiation assemblies 510a (e.g., four columns, six columns, etc.), and/or the radiation assemblies 510a can be arranged in other suitable configurations. For example, the radiation assemblies 510a can be carried by a housing (e.g., the housing 102 of FIGS. 1A-1C) and directed generally inward toward an enclosed space defined by the housing.

Similar to the apparatus 500 discussed above with reference to FIGS. 1A-1D, the apparatus 500 of FIG. 5A can emit high intensity focused UVB radiation to facilitate vitamin D production in the skin during relatively short phototherapy sessions. For example, the apparatus 500 can provide a sufficient amount of irradiation during a one-minute phototherapy session to stimulate the production of a weekly or monthly dose of vitamin D. The exposure time of each phototherapy session can be selected based on the on the user's skin type (e.g., as defined by the Fitzpatrick scale) and the intensity of the radiation assemblies 510a. For example, the lighter the user's skin tone, the less exposure time necessary to obtain the desired level of vitamin D synthesis in the user's skin. As another example, the higher the intensity of the irradiation provided by the apparatus 500, the less exposure time necessary to obtain the desired irradiation for vitamin D production. In various embodiments, the duration of the phototherapy sessions can also be selected to at least reduce the likelihood that users experience sunburn after the phototherapy session. For example, the exposure time to UVB irradiation can be limited to a user-specific MED of 1.0 or less (e.g., an MED of 0.75). In other embodiments, the exposure time of apparatus 500 can be determined using other suitable parameters for UVB irradiation and/or vitamin D synthesis.

Figure 5B:
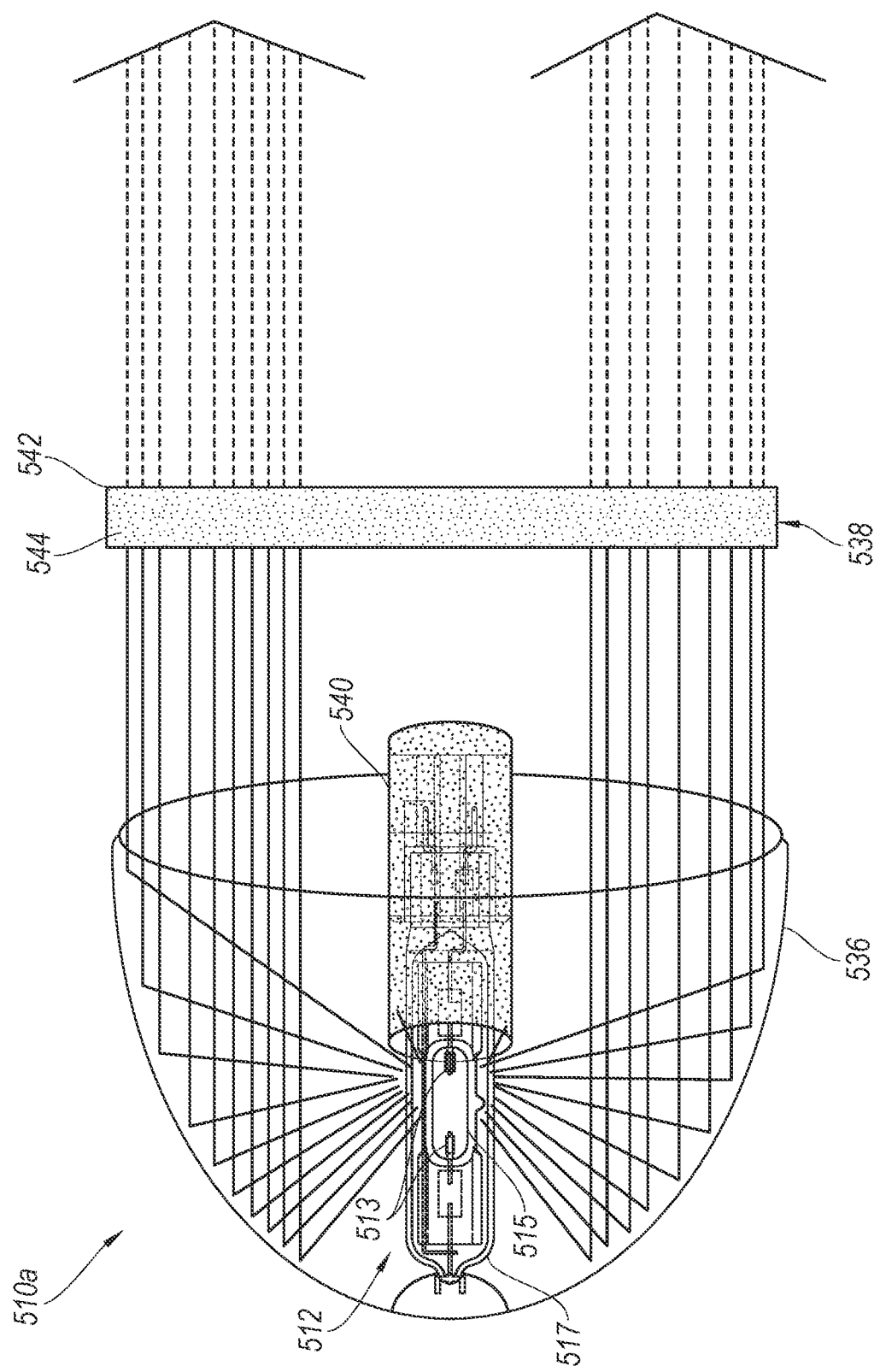
FIG. 5B is an enlarged partially schematic side view of a focused UVB radiation assembly of the phototherapeutic apparatus of FIG. 5A configured in accordance with an embodiment of the present technology.

As shown in FIG. 5A, each radiation assembly 510a can include a radiation source 512, a reflector 536 partially surrounding the radiation source 512, and an optical filter 538 forward of the radiation source 512. FIG. 5B is an enlarged partially schematic side view of a radiation assembly 510a of FIG. 5A configured in accordance with an embodiment of the present technology. As shown in FIG. 5B, the radiation source 512 can emit energy (e.g., UV light; as indicated by the solid lines), and at least some of the energy can contact the reflector 536 (e.g., a mirrored substrate or coating) before exiting the radiation assembly 510a. The reflector 536 can divert or otherwise direct the light forward (e.g., as indicated by the solid lines) toward the filter 538 where light within a predetermined bandwidth (e.g., about 292-302 nm) can exit the radiation assembly 510a (e.g., as indicated by the broken lines). In the illustrated embodiment, the reflector 536 is curved around the radiation source 512 such that the light emitted by the radiation source 512 collaminates upon contact with the reflector 536. The collaminated beam of light can then travel forward toward the filter 538, and pass through the filter 538 at the same angle of incidence (e.g., 0°) to provide substantially uniform filtering of the light.

In the embodiment illustrated in FIG. 5B, the radiation source 512 is a metal-halide lamp, which is a type of HID gas discharge lamp that generates light by producing an electric arc through a gaseous mixture between two electrodes 513 in an arc tube or envelope 515. The arc length (i.e., about the distance between the electrodes 513) of the metal-halide lamp can be relatively small with respect to radiation assembly 510a as a whole such that the metal-halide lamp acts similar to a point source to facilitate collamination of the light. In certain embodiments, for example, the electrodes 513 can be spaced apart from each other such that the metal-halide lamp has an arc length of about 10-12 mm (e.g., about 11 mm, about 11.5 mm, etc.). In other embodiments, the metal-halide lamp can have larger or smaller arc lengths depending on the configuration of the metal-halide lamp and the sizing of the other components of the radiation assembly 510a (e.g., the reflector 536). Metal-halide lamps typically have a ramp up period to warm up to an operating temperature. Therefore, in certain embodiments, the radiation assembly 510a can include shutters or other covers (not shown) that temporarily enclose or insulate the radiation source 512 for a time period (e.g., about 2 minutes, about 1 minute, etc.) to allow the metal-halide lamp to quickly ramp up to its operating temperature.

In various embodiments, the gas mixture in the arc tube 515 can be selected to increase the UVB content of the emissions of the metal-halide lamp. For example, the gas mixture can be doped to generate about 6% of the total emissions in the UVB range (e.g., about 280-315 nm) in comparison to normal tanning bed lamps that have about 1% of their emissions in the UVB range. Suitable gas mixtures for increased UVB content are available from Heraeus Nobelight of Plainview, N.Y. The increased UVB content of the emissions can increase the intensity of the UVB emitted by the radiation assembly 510a, and therefore may decrease the overall exposure time necessary to achieve a desired vitamin D dose.

As shown in FIG. 5B, the radiation assembly 510a can further include an optional cover or shield 540 between the radiation source 512 and the filter 538 to at least substantially prevent light from exiting the radiation assembly 510a without first propagating off of the reflector 538. In the illustrated embodiment, for example, the shield 540 is a tubular body spaced apart from the radiation source 512 (e.g., using stand-offs similar to the stand-offs 114 of FIG. 1D) and positioned around a portion of the radiation source 512 forward of the arc tube 515. The shield 540 can block light that propagates forward from the arc tube 513 such that the light first contacts the reflector 538 before exiting the radiation assembly 510a. In this manner, the shield 540 can promote collamination of light by the reflector 536 before the light contacts the filter 538. In other embodiments, the shield 540 can have other suitable shapes or configurations that prevent light from propagating directly forward through the filter 538.

The filter 538 can be a narrow pass filter that prevents UVB radiation outside of a predetermined bandwidth from passing through the filter 538. For example, the filter 538 can at least substantially block UVB radiation outside of a 10 nm spectrum centered at about 297 nm (i.e., about 292-302 nm). In other embodiments, the filter 538 can at least substantially block UVB radiation outside of a narrower bandwidth (e.g., a 6 nm spectrum, an 8 nm spectrum, etc.), a wider bandwidth (e.g., a 12 nm spectrum), and/or the spectrum can be centered around another suitable UVB wavelength (e.g., 298 nm, 300 nm, 302 nm, etc.).

As shown in FIG. 5B, the filter 538 can include a substrate 542 (e.g., glass, plastic, etc.) and at least one interference coating 544 applied to the substrate 542. For example, the coating 544 can be sprayed onto the substrate 542 and/or otherwise disposed on the substrate 542 using methods known to those skilled in the art. In certain embodiments, the substrate 542 can be made from a material (e.g., glass) that blocks at least some of the UV light emitted by the radiation source 512. For example, the substrate 542 can be made from an absorption glass that blocks UV radiation below, for example, about 290 nm. The coating 544 (e.g., one or more optical coatings) can be applied to the substrate 542 to provide additional filtering of energy outside of the predetermined bandwidth. For example, the coating 544 may provide a higher degree of precision in filtering the energy outside of a predetermined spectrum than provided by the substrate 542 such that the substrate 542 and the coating 544 together form a narrow pass filter. In certain embodiments, for example, a first coating can be applied to the substrate 542 to block light with wavelengths less than the minimum wavelength of the predetermined spectrum, and a second coating can be applied to the substrate 542 to block light with wavelengths higher than the maximum wavelength of the predetermined spectrum. In other embodiments, the substrate 542 or the coating 544 can alone provide suitable filtering of light outside of the predetermined spectrum. Substrates 542 and coatings 544 that provide at least some filtering of UV radiation outside of a predetermined spectrum are available from Schott of Elmsford, New York.

In various embodiments, other portions of the radiation assembly 510a can include an interference coating that blocks at least some radiation outside of the desired wavelength spectrum. For example, an outer bulb 517 of the metal-halide lamp can include an interference coating that blocks at least some UV radiation outside the UVB spectrum from exiting the metal-halide lamp. A coating, for example, can be applied to the outer bulb 517 to block some of the emissions in the UVC range (e.g., about 100-280 nm) and inhibit ozone from forming. In this embodiment, the radiation source 512 narrows the spectrum of light exposed to the filter 538, and therefore the filter 538 need only be concerned with further narrowing the bandwidth of light permitted to pass through the filter 538.

FIG. 5C is an enlarged partially schematic side view of a focused UVB radiation assembly 510b ("radiation assembly 510b") configured in accordance with another embodiment of the present technology. The radiation assembly 510b can include features generally similar to the features of the radiation assembly 500a described above with respect to FIG. 5B. For example, the radiation assembly 510b includes the UV radiation source 512, the reflector 536 at least partially surrounding the radiation source 512, the filter 538, and the shield 540 between the radiation source 512 and the filter 538. The radiation source 512 can be a metal-halide lamp that functions substantially as a point source relative to the radiation assembly 510b, and emits energy radially outward (e.g., as indicated by the solid lines of FIG. 5C). The shield 540 can deflect or otherwise redirect energy emitted from the radiation source 512 back toward the reflector 536 such that the reflector 536 can at least substantially collaminate the light before it passes through the filter 538. In the embodiment illustrated in FIG. 5C, the shield 540 has a substantially hemispherical shape and is connected to a base portion 546 of the metal-halide lamp with a stand-off 548 (e.g., a rod, a bar, etc.) that extends from the base portion 546 to the shield 540. In other embodiments, the shield 540 can have other suitable configurations to block energy from exiting the radiation assembly 510b without first contacting the collaminating reflector 536.

Figure 6:
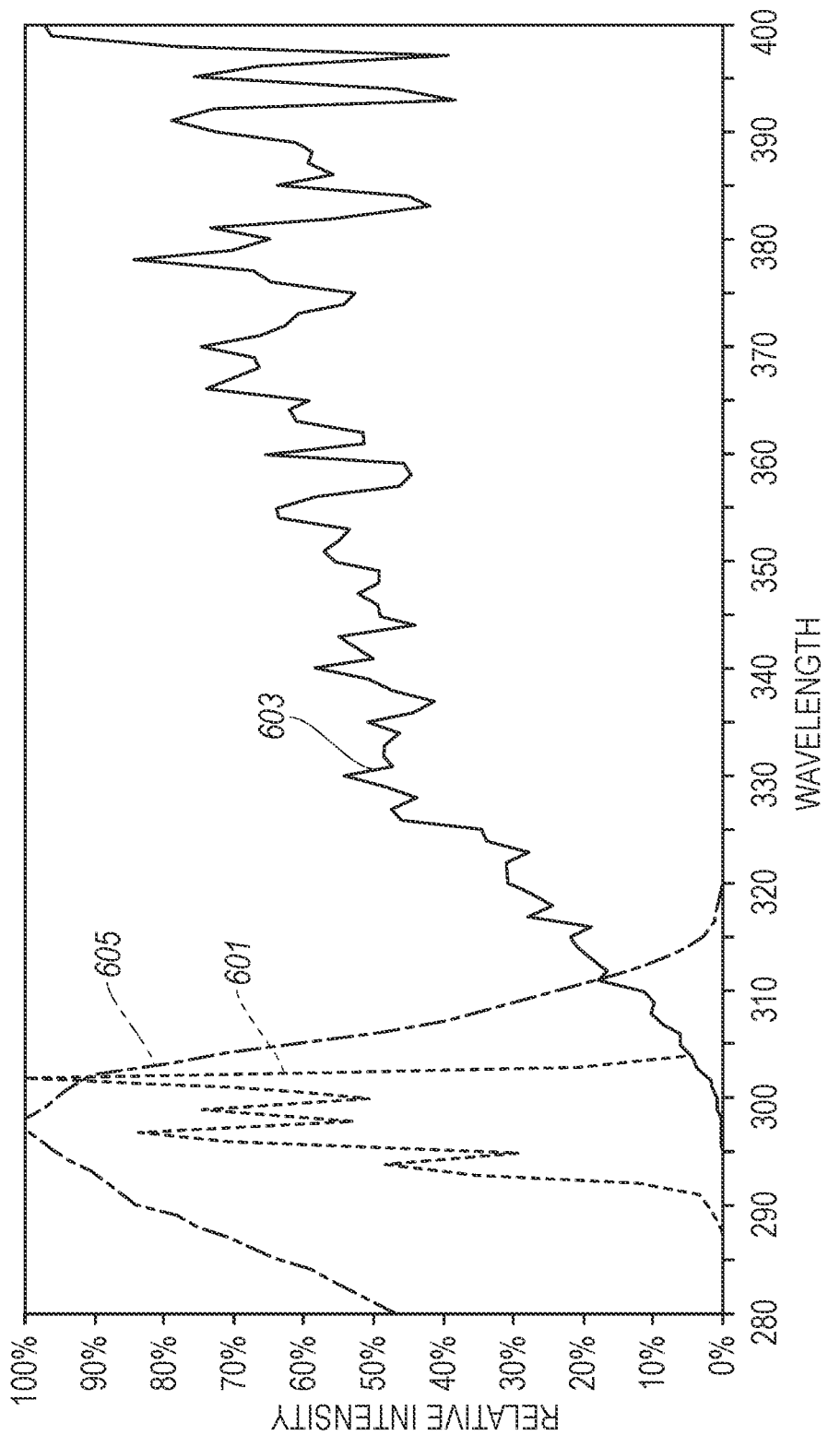
FIG. 6 is an exemplary graphical representation of the relative radiation intensity of a focused UVB radiation assembly with a metal halide UV source configured in accordance with the present technology compared to the relative radiation intensity of the sun.

FIG. 6 is an exemplary graphical representation of the relative radiation intensity of a focused UVB radiation assembly with a metal-halide UV source (e.g., the radiation assemblies 510a and 510b described above with respect to FIGS. 5A-5C) compared to the relative radiation intensity of the sun. More specifically, curve 601 (shown as a broken line) represents the intensity of the metal-halide radiation assembly, curve 603 (shown as a solid line) represents the intensity of the sun measured at about noon during the summer in Melbourne, Australia, and curve 605 represents the action spectrum of UV radiation known to promote vitamin D production in the skin. As illustrated in FIG. 6, the metal-halide radiation assembly emits UV light primarily between about 292-302 nm (e.g., focused at about 297 nm), and therefore most of the emissions are within the action spectrum 605 for vitamin D production. In contrast, despite being measured at one of the sun's peak energy times and locations, solar energy has a relatively low intensity of UV light within the UVB spectrum (i.e., about 280-315 nm), and has a relatively high intensity of UV light in the UVA spectrum (i.e., about 315-400 nm). For example, 99.7% of the UV emissions from the metal-halide radiation assembly can be within the focused UVB range, whereas only about 3.4% of the solar emissions are within the focused UVB range. Accordingly, phototherapeutic apparatuses that include the metal-halide radiation assemblies depicted in FIG. 6 can emit UV energy with a much higher UVB content and intensity than normal sun exposure. This concentrated UVB radiation can be used to promote vitamin D production in the skin, and do so in a much shorter exposure time than can be provided by the sun. For example, in certain embodiments, the UVB irradiation that is provided by about 38 minutes of sun exposure (at peak times) can be provided by less than a minute (e.g., 58 seconds) of exposure to the metal-halide radiation assembly. In addition, the high intensity of the UVB radiation provided by the metal-halide radiation assembly can facilitate significantly more vitamin D synthesis in the skin than the lower intensity UVB radiation provided by the sun. In certain embodiments, for example, the metal-halide radiation assembly can provide at least three times the production of vitamin D in the skin than can be obtained from the sun (e.g., 74,500 IU via focused UVB radiation compared to 20,000 IU equivalent via solar energy). Moreover, despite the high concentration of UVB radiation, the focused UVB radiation assembly exposes a subject (e.g., a human patient) to less overall UV energy during a phototherapy session than sun exposure (e.g., 62 times less UV energy than the sun) because much of the UV radiation outside the predetermined spectrum is filtered out by the focused UVB radiation assembly (e.g., via the filter 538 of FIGS. 5A-5C). Accordingly, the focused UVB radiation assembly provides a substantially more efficient means for producing vitamin D in the skin than the sun, and does so without the geographic and weather-dependent initiations of sun exposure.

Figure 7:
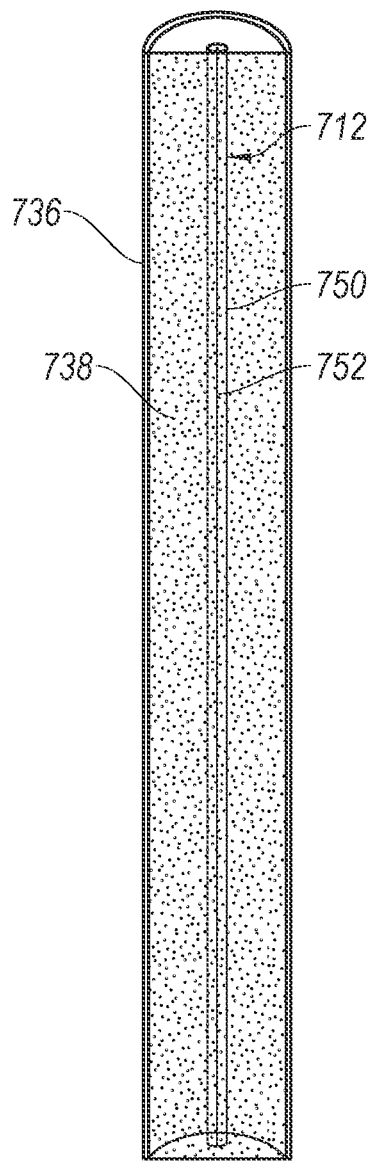
FIG. 7 is an elevational front view of a focused UVB radiation assembly for a phototherapeutic apparatus configured in accordance with a further embodiment of the present technology.

FIG. 7 is a front elevational view of a focused UVB radiation assembly 710 ("radiation assembly 710") for a phototherapeutic apparatus configured in accordance with a further embodiment of the present technology. The radiation assembly 710 can include several features generally similar to the features of the radiation assemblies 110, 510a and 510b described above with respect to FIGS. 1D, 5B and 5C. For example, the radiation assembly 710 can include a UV radiation source 712, a reflector 736 positioned behind and partially around the radiation source 712, and a filter 738 forward of the radiation source 712. In the illustrated embodiment, radiation source 712 is a xenon lamp 750, which produces a pulsed or continuous beam of light 752 in a tube by passing electricity through ionized xenon gas at high pressure. The xenon lamp 750 can be coupled to a power source (e.g., a 16 kW power source; not shown), and forced air can be supplied from one or both ends of the radiation assembly 710 for cooling. Xenon lamps inherently emit energy with a high UVB content, and therefore facilitate the focused UVB irradiation provided by the radiation assembly 710. Suitable xenon lamps (e.g., pulsed linear xenon lamps) for the radiation assembly 710 are available from Heraeus Nobelight GmbH of Hanau, Germany.

As shown in FIG. 7, the xenon lamp 750 can be an elongated structure that emits a linear beam of UV light 752. For example, the xenon lamp 750 can have a diameter of about 8 mm and a length of about 165 mm such that can extend along the height or length of a phototherapeutic apparatus (e.g., the phototherapeutic apparatuses 100 and 500 of FIGS. 1A and 5A). In other embodiments, the xenon lamp can be longer or shorter length and/or have smaller or larger diameters. The reflector 736 (e.g., a barrel reflector) can also be an elongated structure that extends along the length of the xenon lamp 750 to direct light forward toward the filter 738 where filtered UVB light exits the radiation assembly. The filter 738 can include an absorption glass or other type of substrate that blocks energy below a certain wavelength (e.g., below about 290 nm) and an interference coating can block energy with higher wavelengths (e.g., above about 306 nm).

The radiation assembly 710 with the xenon lamp 750 can be used in conjunction with or in lieu of the metal-halide lamps in the phototherapeutic apparatuses 100 and 500 described above. For example, the radiation assembly 710 can be carried by a column (e.g., one of the columns 530 of the phototherapeutic apparatus of FIG. 5A), and the xenon lamp 750 can be configured to generate a beam of light that extends substantially along the length of the column. During operation, one or more of the radiation assemblies 710 can be rotated around a base (e.g., the central portion 534 of the base 532 of FIG. 5A) to provide focused UVB radiation to a subject (e.g., a human patient) standing on the base. In other embodiments, one or more radiation assemblies 710 can be incorporated into a housing (e.g., the housing 102 of FIG. 1A) and configured to direct emissions toward an enclosed space provided by the housing.

Figure 8:
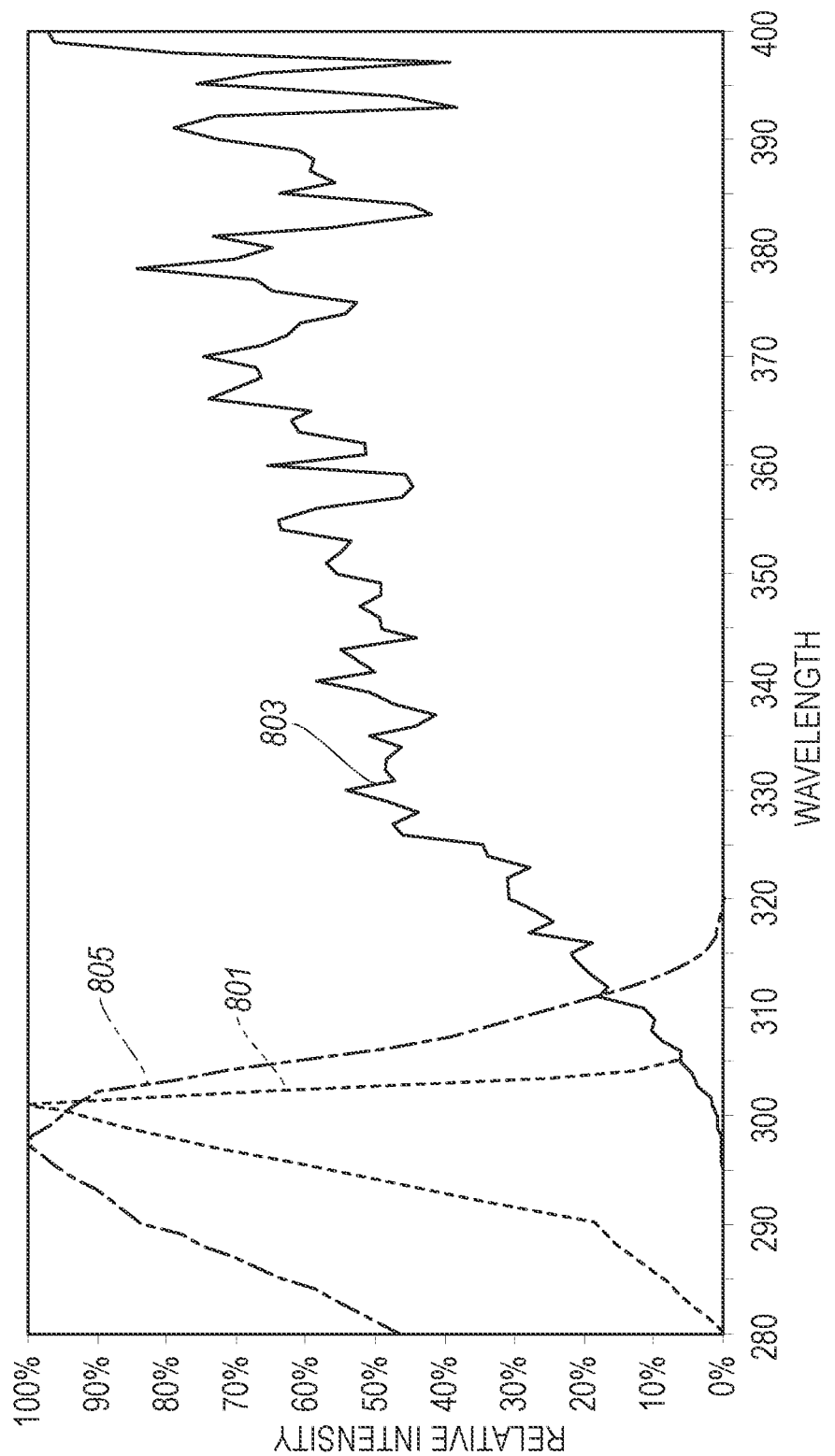
FIG. 8 is an exemplary graphical representation of the relative radiation intensity of a focused UVB radiation assembly with a pulsed xenon UV source configured in accordance with the present technology compared to the relative radiation intensity of the sun.

FIG. 8 is an exemplary graphical representation of the relative radiation intensity of a focused UVB radiation assembly with a pulsed xenon UV source (e.g., the radiation assembly 710 of FIG. 7) compared to the relative radiation intensity of the sun. Curve 801 (shown as a broken line) represents the intensity of the xenon lamp radiation assembly, curve 803 (shown as a solid line) represents solar intensity (measured at about noon during the summer in Melbourne, Australia), and curve 805 represents the action spectrum for vitamin D production in the skin. As shown in FIG. 8, the solar spectrum (as defined by the area under the curve 803) has very little output (e.g., about 3.4%) within vitamin D action spectrum 805. In contrast, almost all of the output (e.g., over 98%) of the xenon lamp radiation assembly is within the vitamin D action spectrum 805. In addition, the intensity of UVB radiation provided by the xenon lamp radiation assembly is much higher than that provided by solar energy. Accordingly, the xenon lamp radiation assembly can provide focused UVB radiation within the vitamin D action spectrum 805 that facilitates vitamin D synthesis in the skin in significantly shorter exposure times than can be provided by solar energy. For example, the UVB radiation provided by one xenon lamp radiation assembly in less than one minute (e.g., 57 seconds) is equivalent to over 30 minutes (e.g., 38 minutes) of sun exposure.

In various embodiments, the phototherapeutic apparatuses 100 and 500 described above can include other types of UV radiation sources (e.g., radiation sources 112, 512 and 712 of FIGS. 1D, 5B, 5C and 7) that, in combination with optional filters, can provide focused UVB irradiation within a predetermined spectrum. For example, the UV radiation source can be comprised of a plurality of LEDs (e.g., thousands of LEDs) that emit light at a particular wavelength (e.g., 295 nm, 297 nm, 300 nm, etc.). Suitable LEDs are available from, for example, Sensor Electronic Technology, Inc. of Columbus, South Carolina. In certain embodiments, one or more LEDs can be arranged in individual radiation assemblies (e.g., similar to the metal-halide lamps of FIGS. 5A-5C). In other embodiments, the LEDs can be arranged in elongated rows and/or columns extending along the length of the phototherapeutic apparatus (e.g., similar to the xenon lamp of FIG. 7). The substantially monochromatic output of the LEDs may limit the amount of filtering necessary to provide UVB radiation within a predetermined spectrum. In addition, LEDs have relatively low power consumption (e.g., in comparison to HID lamps), and therefore inherently provide power savings. In further embodiments, the UV radiation source can be comprised of excimer lamps that can emit light within a narrow spectral range (e.g., the excimer lamps available from Ushio of Cypress, Calif.) and/or other suitable UV radiation sources that can be manipulated for focused UVB radiation.

From the foregoing, it will be appreciated that specific embodiments of the technology have been described herein for purposes of illustration, but that various modifications may be made without deviating from the disclosure. For example, various embodiments disclosed herein include filters that focus UVB radiation around 297 nm. However, in other embodiments, the filters can focus UVB radiation around other wavelengths that enable vitamin D production in the skin and/or provide therapeutic effects for other diseases or disorders treated via the skin (e.g., psoriasis, eczema, etc.). Certain aspects of the new technology described in the context of particular embodiments may be combined or eliminated in other embodiments. For example, the metal-halide UV source described in FIGS. 5A-5C and/or the xenon UV source described in FIG. 7 can be used in lieu of or in conjunction with the UV radiation source for the phototherapeutic apparatus of FIGS. 1A-1C. Additionally, although advantages associated with certain embodiments of the new technology have been described in the context of those embodiments, other embodiments may also exhibit such advantages and not all embodiments need necessarily exhibit such advantages to fall within the scope of the technology. Accordingly, the disclosure and associated technology can encompass other embodiments not expressly shown or described herein.

I claim:

1. A phototherapeutic apparatus, comprising:
   an ultraviolet (UV) radiation assembly comprising:
      a UV radiation source carried by a housing; and
      a reflector positioned forward of the UV radiation source to direct UV energy emitted by the UV radiation source forward toward an irradiation zone, the UV energy contacting the reflector forward of the UV radiation source,
      wherein the UV radiation source is configured to emit UV radiation having wavelengths between 290 nm and 310 nm to stimulate vitamin D production in skin; and
   a controller communicatively coupled to the UV radiation source and configured to cause the phototherapeutic apparatus to limit UV radiation of the phototherapeutic apparatus to less than a user-specific minimum erythemal dose ("MED") based on a skin tone associated with a user in the irradiation zone by adjusting a duration of an exposure period.

2. The phototherapeutic apparatus of claim 1 wherein the UV radiation source comprises a light emitting diode (LED).

3. The phototherapeutic apparatus of claim 1, further comprising a housing carrying the UV radiation source, wherein:
   the UV radiation source comprises a plurality of LEDs arranged in a plurality of columns across the housing; and
   the reflector comprises a plurality of reflectors corresponding to the plurality of LEDs, the plurality of reflectors positioned forward of the corresponding plurality of LEDs, wherein the plurality of reflectors are configured to direct UV energy emitted by the corresponding plurality of LEDs forward toward the irradiation zone, the UV energy contacting the plurality of reflectors forward of the plurality of LEDs.

4. The phototherapeutic apparatus of claim 1 wherein the UV radiation source further comprises a filter positioned forward of the UV radiation source.

5. The phototherapeutic apparatus of claim 1 wherein:
   the UV radiation source comprises a plurality of UV radiation sources; and
   the UV radiation source further comprises a plurality of filters corresponding to the plurality of UV radiation sources, the plurality of filters positioned forward of the corresponding UV radiation sources.

6. The phototherapeutic apparatus of claim 1 wherein the UV radiation source comprises one or more LEDs configured to emit the UV radiation having wavelengths between 290 nm and 305 nm.

7. The phototherapeutic apparatus of claim 1 wherein the phototherapeutic apparatus is part of a phototherapy system, the phototherapy system comprising a user interface communicatively coupled to the controller and configured to receive user-specific information related to parameters that affect vitamin D synthesis in a human patient.

8. The phototherapeutic apparatus of claim 7 wherein the user interface is directly coupled or wirelessly coupled to the phototherapeutic apparatus.

9. The phototherapeutic apparatus of claim 1 wherein the controller is configured to receive user-specific information via a website or a smart phone application.

10. The phototherapeutic apparatus of claim 7 wherein the user interface is configured to receive feedback from the user regarding a previous phototherapy session provided by the phototherapeutic apparatus or a remote phototherapeutic apparatus communicatively coupled to the user interface.

11. A method of delivering ultraviolet (UV) radiation to stimulate vitamin D production via irradiation of skin, the method comprising:
   emitting UV energy with one or more light emitting diodes (LEDs) carried by a housing of a phototherapeutic apparatus;
   directing, via one or more reflectors, the UV energy forward from the one or more LEDs toward an irradiation zone, wherein the UV energy transmitted from the phototherapeutic apparatus to the irradiation zone is within a predefined spectrum between 290 nm and 310 nm;
   terminating the transmission of the UV energy after a user has been exposed to less than a user-specific minimum erythemal dose ("MED") based on user-specific information.

12. The method of claim 11, further comprising receiving the user-specific information related to parameters that affect vitamin D synthesis in a human patient from a user interface communicatively coupled to the phototherapeutic apparatus.

13. The method of claim 11, further comprising filtering the UV energy with at least one filter positioned between at least one of the LEDs and the irradiation zone.

14. The method of claim 11 wherein the UV energy transmitted from the phototherapeutic apparatus to the irradiation zone is at least substantially focused within at most a 10 nm spectrum centered at about 297 nm.

15. The method of claim 11, further comprising:
   receiving a user input related to at least one of vitamin D dosage or skin type, wherein the vitamin D dosage is an amount of vitamin D that stimulation by the UV energy is expected to produce in the skin of a human patient; and
   selecting a predetermined time period of the vitamin D dosage based on the user input.

16. A phototherapeutic apparatus, comprising:
   an ultraviolet (UV) radiation assembly comprising:
      a housing; and
      a UV radiation source carried by the housing and positioned to emit UV radiation toward an irradiation zone, wherein the UV radiation assembly is configured to emit the UV radiation at wavelengths between 290 nm and 310 nm to stimulate vitamin D production in skin; and
   a controller communicatively coupled to the UV radiation assembly and configured to cause the phototherapeutic apparatus to limit UV radiation of the phototherapeutic apparatus to less than a user-specific minimum erythemal dose ("MED") based on a skin tone associated with a user in the irradiation zone by adjusting a duration of an exposure period.

17. The phototherapeutic apparatus of claim 16 wherein the UV radiation source comprises a light emitting diode (LED).

18. The phototherapeutic apparatus of claim 16 wherein the UV radiation source comprises a plurality of LEDs arranged in a plurality of columns across the housing.

19. The phototherapeutic apparatus of claim 16 wherein the phototherapeutic apparatus is part of a phototherapy system, the phototherapy system comprising a user interface communicatively coupled to the controller and configured to receive user-specific information related to parameters that affect vitamin D synthesis in a human patient.

20. The phototherapeutic apparatus of claim 16 wherein the controller is configured to receive user-specific information via a website or a smart phone application.

* * * * *